(12) United States Patent
Koya et al.

(10) Patent No.: US 7,750,042 B2
(45) Date of Patent: *Jul. 6, 2010

(54) PACLITAXEL ENHANCER COMPOUND

(75) Inventors: Keizo Koya, Chestnut Hill, MA (US); Lijun Sun, Harvard, MA (US); Shoujun Chen, Bedford, MA (US); Noriaki Tatsuta, Lexington, MA (US); Yaming Wu, Lexington, MA (US); Mitsunori Ono, Lexington, MA (US); Zhi-Qiang Xia, Acton, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/077,729

(22) Filed: Mar. 20, 2008

(65) Prior Publication Data

US 2008/0242702 A1    Oct. 2, 2008

Related U.S. Application Data

(60) Division of application No. 11/244,427, filed on Oct. 5, 2005, now Pat. No. 7,368,473, which is a continuation of application No. 10/803,798, filed on Mar. 18, 1004, now Pat. No. 7,001,923, which is a continuation of application No. 10/193,639, filed on Jul. 10, 2002, now Pat. No. 6,762,204.

(60) Provisional application No. 60/304,252, filed on Jul. 10, 2001, provisional application No. 60/361,936, filed on Mar. 6, 2002.

(51) Int. Cl.
*A61K 31/335* (2006.01)
*A61K 31/20* (2006.01)
*C07C 327/38* (2006.01)
*C07C 243/18* (2006.01)

(52) U.S. Cl. .................... 514/449; 514/559; 564/74; 564/148; 564/149

(58) Field of Classification Search ............... 514/449, 514/599; 564/74, 148, 149
See application file for complete search history.

(56) References Cited

U.S. PATENT DOCUMENTS

| | | | |
|---|---|---|---|
| 3,357,956 A * | 12/1967 | Frazer .................... 528/381 |
| 4,012,360 A | 3/1977 | Schwarzenbach et al. |
| 4,822,777 A | 4/1989 | Abra |
| 5,498,421 A | 3/1996 | Grinstaff et al. |
| 5,560,933 A | 10/1996 | Soon-Shiong et al. |
| 5,665,382 A | 9/1997 | Grinstaff et al. |
| 5,739,686 A | 4/1998 | Naughton et al. |
| 5,840,746 A | 11/1998 | Ducharme et al. |
| 5,916,596 A | 6/1999 | Desai et al. |
| 6,013,836 A | 1/2000 | Hsu et al. |
| 6,096,331 A | 8/2000 | Desai et al. |
| 6,172,108 B1 | 1/2001 | Vega et al. |

(Continued)

FOREIGN PATENT DOCUMENTS

AU    2006/228035 A1    11/2006

(Continued)

OTHER PUBLICATIONS

Chuyguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984).

(Continued)

*Primary Examiner*—Yong Chu
(74) *Attorney, Agent, or Firm*—Foley & Lardner LLP; Steven G. Davis

(57) ABSTRACT

One embodiment of the present invention is a compound represented by the Structural Formula (I):

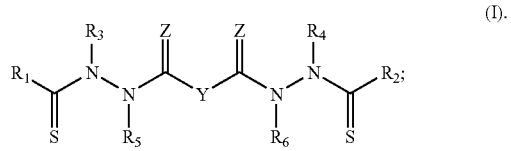

Y is a covalent bond of a substituted or unsubstituted straight chained hydrocarbyl group. In addition, Y, taken together with both >C=Z groups to which it is bonded, is a substituted or unsubstituted aromatic group. Preferably, Y is a covalent bond or —C($R_7R_8$)—.

$R_1$ is an aliphatic group, a substituted aliphatic group, a non-aromatic heterocyclic group, or a substituted non-aromatic heterocyclic group, $R_2$-$R_4$ are independently —H, an aliphatic group, a substituted aliphatic group, a non-aromatic heterocyclic group, a substituted non-aromatic heterocyclic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

$R_5$-$R_6$ are independently —H, an aliphatic group, a substituted aliphatic group, an aryl group or a substituted aryl group.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2-C6 substituted or unsubstituted alkylene group.

Z is =O or =S.

Also disclosed are pharmaceutical compositions comprising the compound of the present invention and a pharmaceutically acceptable carrier or diluent.

32 Claims, 26 Drawing Sheets

U.S. PATENT DOCUMENTS

| | | |
|---|---|---|
| 6,172,188 B1 | 1/2001 | Thastrup et al. |
| 6,214,863 B1 | 4/2001 | Bissery et al. |
| 6,235,787 B1 | 5/2001 | Broadhurst et al. |
| 6,365,745 B1 | 4/2002 | Matsui et al. |
| 6,399,659 B2 | 6/2002 | Usui et al. |
| 6,435,787 B1 | 8/2002 | John |
| 6,455,515 B2 | 9/2002 | Gypser et al. |
| 6,506,405 B1 | 1/2003 | Desai et al. |
| 6,537,579 B1 | 3/2003 | Desai et al. |
| 6,656,971 B2 | 12/2003 | Wu et al. |
| 6,703,426 B1 | 3/2004 | Miles et al. |
| 6,749,868 B1 | 6/2004 | Desai et al. |
| 6,753,006 B1 | 6/2004 | Desai et al. |
| 6,762,204 B2 | 7/2004 | Koya et al. |
| 6,800,660 B2 | 10/2004 | Koya et al. |
| 6,825,235 B2 | 11/2004 | Chen et al. |
| 6,924,312 B2 | 8/2005 | Koya et al. |
| 7,001,923 B2 * | 2/2006 | Koya et al. .......... 514/599 |
| 7,037,940 B2 | 5/2006 | Koya et al. |
| 7,074,952 B2 | 7/2006 | Chen et al. |
| 7,250,432 B2 | 7/2007 | Kwon et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 2002/0198160 A1 | 12/2002 | Everitt et al. |
| 2004/0022869 A1 | 2/2004 | Chen et al. |
| 2004/0225016 A1 | 11/2004 | Koya et al. |
| 2004/0235813 A1 | 11/2004 | Wanker et al. |
| 2005/0154039 A1 | 7/2005 | Glacera Contour |
| 2006/0135595 A1 | 6/2006 | Koya et al. |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2006/0270873 A1 | 11/2006 | Chen et al. |
| 2006/0281811 A1 | 12/2006 | Chen et al. |
| 2007/0088057 A1 | 4/2007 | Lunsmann et al. |
| 2008/0089950 A1 | 4/2008 | Chen et al. |
| 2008/0118562 A1 | 5/2008 | Koya |
| 2008/0119440 A1 | 5/2008 | Koya |
| 2008/0146842 A1 | 6/2008 | Chen et al. |
| 2008/0176828 A1 | 7/2008 | Williams et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0023736 A1 | 1/2009 | Koya et al. |
| 2009/0042991 A1 | 2/2009 | Barsoum et al. |
| 2009/0093538 A1 | 4/2009 | Bertin et al. |
| 2009/0137682 A1 | 5/2009 | Dahl |

FOREIGN PATENT DOCUMENTS

| | | |
|---|---|---|
| DE | 2037257 | 2/1972 |
| EP | 1454628 A | 9/2004 |
| EP | 1493445 A | 1/2005 |
| EP | 1406869 B1 | 9/2006 |
| EP | 1 731 148 A | 12/2006 |
| FR | 2097737 | 4/1972 |
| GB | 1272920 | 5/1972 |
| JP | 50-91056 | 7/1975 |
| JP | 63-267752 A | 11/1988 |
| JP | 07-165693 A | 6/1995 |
| JP | 10-501215 A | 2/1998 |
| WO | WO 94/10995 | 5/1994 |
| WO | WO 99/34796 | 7/1999 |
| WO | WO 03/006428 A | 1/2003 |
| WO | WO 03/006429 A1 | 1/2003 |
| WO | WO 03/006430 A | 1/2003 |
| WO | WO 03/047524 A2 | 6/2003 |
| WO | WO 2004/064826 A1 | 8/2004 |
| WO | WO 2004/072051 A1 | 8/2004 |
| WO | WO 2005/028475 A2 | 3/2005 |
| WO | WO 2005/097758 A1 | 10/2005 |
| WO | WO 2006/009940 A1 | 1/2006 |
| WO | WO 2006/033913 | 3/2006 |
| WO | WO 2006/055747 A2 | 5/2006 |
| WO | WO 2006/062732 A2 | 6/2006 |
| WO | WO 2006/089177 A2 | 8/2006 |
| WO | WO 2006/113493 A2 | 10/2006 |
| WO | WO 2006/113572 | 10/2006 |
| WO | WO 2006/113695 | 10/2006 |
| WO | WO 2006/124736 A2 | 11/2006 |
| WO | WO 2007/021881 A2 | 2/2007 |
| WO | WO 2007/139955 A2 | 12/2007 |
| WO | WO 2008/024298 A1 | 2/2008 |
| WO | WO 2008/024299 A2 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033449 A2 | 3/2008 |
| WO | WO 2008/033494 A2 | 3/2008 |
| WO | WO 2008/082579 A1 | 7/2008 |
| WO | WO 2008/136976 A2 | 11/2008 |
| WO | WO 2009/020631 A2 | 2/2009 |
| WO | WO 2009/064374 A2 | 5/2009 |
| WO | WO 2009/073147 A2 | 6/2009 |
| WO | WO 2009/073148 A2 | 6/2009 |

OTHER PUBLICATIONS

"Remarks" paper as submitted by applicant's attorney, 2 pp., Jun. 23, 2004.

Stalteri, M.A., et al., "Site-specific conjugation and labelling of prostate antibody 7E11C5.3 (CYT-351) with technetium-99m," *European Journal of Nuclear Medicine* 24(6):651-654, (1997).

Twomey, D., "Anticancer Agents-IX. Derivatives of Pyridine, Pyridazine and Phthalazine," *Proceedings of the Royal Irish Academy*, vol. 74, Sect. B:37-52,(1974).

Schwarz et al., CA77:48081, 1972.

Rupp, Walter, CA76:126992, 1972.

Barry, V. C. , et al., "Anticancer Agents—III. Synthesis and Anticancer Activity of Some Bis-Thiosemicarbazones and Thoiosemicarbazides," *Proc. R.I.A.* 65:309-324 (1967).

O'Callaghan, C. N., "Anticancer Agents—X. Cyclisation of 1-Acyl-4-Alkylthiosemicarbazide Derivatives to 1,2,4-Triazoline-3-Thiones in the Presence of Hydrazine," *Proc. R.I.A.* 74:455-461 (1974).

Bräuniger, H., "Hydrazide and Hydrazidderivate von Dicarbonsäuren," Pharmaceutical-Chemical Institute of University of Rostock, Supplied by the "British Library," *Pharmazie* 25(5-6) 279-283 (1970).

Al-Talib, M. et al., "Diacyl Acid Dihydrazides," *Magnetic Resonance in Chemistry* 28:1072-1078 (1990).

Chuiguk, V.A., and Nemazanyi, A.G., "Mesoionic Methine Dyes Of Biquaternary Salts Of Diheteroaryl Methanes—Derivatives Of 1, 3, 4—oxa (thia) Diazoles and 1, 2, 4—Triazoles," *Kiev. Gos. Univ., Kiev, USSR, Ukrainskii Khimicheskii Zhurnal, Russian Edition*, 50(5):519-524 (1984). Abstract, Accession No. 1984:630420, HCAPLUS Database.

Barrett, William G. and McKay, Donald, "Decomposition and Cycloaddition Reactions of Some Bis(azodicarbonyl) Compounds," *Journal of Chem. Soc.* (4):1046-1052 (1975).

Mitsui Toatsu Chem. Inc., Abstract of Japanese Patent No. 308024, published Dec. 25, 1986. from Derwent Publications Ltd.

Honshu Paper Mfg. Co. Ltd, Abstract of Japanese Patent No. 182050, published Feb. 13, 1996.

Molina, P., et al., XP-01118868 "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-

Bis[4,5-dihydro-5-(2-hydroxyethylimino)-4-methyl-1,3,4-thiadiazole]," *J. Chem. Soc. Perkin Trans. I* 5:1159-1166 (1991).
Molina, P., et al., XP-001118802 "Preparation of a Novel Type of Ligands Incorporating Two or Three 1,3,4-Thiadiazole Units," *Heterocycles* 36(6):1263-1278 (1993).
Rao et al., Cancer, vol. 106, No. 2, 2006, pp. 375-382.
Asahi Chemical Ind. KK. Abstract of Japanese Patent No. 50-91056, Accession No. 47521Y/27 (1975).
Merlin, J.L., et al., "In vitro Comparative Evaluation of Trastuzumab (Herceptin®) Combined with Paclitaxel (Taxol®) or Docetaxel (Taxotere®) in HER2-Expressing Human Breast Cancer Cell Lines," *Annals of Oncology* 13:1743-1748 (2002).
"The Merck Manual," Chapter 14: Principles of Cancer Therapy, 1999 Merck Research Laboratories, pp. 987-995 (1999), XP002477370.
Abuchowski, A., et al., "Alteration of Immunological Properties of Bovine Serum Albumin by Covalent Attachment of Polyethylene Glycol," The *Journal of Biological Chemistry* 252(11):3578-3581 (1977).
Ashburner, M. and Bonner, J.J., " The Induction of Gene Activity in *Drosophila* by Heat Shock," *Cell*, 17: 241-254 (1979).
Auluck, P.K., et al., "Chaperone Suppression of α-Synuclein Toxicity in a *Drosophila* Model for Parkinson's Disease," *Science*, 295: 865-868 (2002).
Bahceci, et al., "Reactions of amidines with some carboxylic acid hydrazides," Indian Journal of Chemistry Section B, vol. 44B, 2005, pp. 568-572, XP009083365, p. 569, Scheme 1.
Balkwill, F. et al., "Inflammation and Cancer: Back to Virchow?" *The Lancet*, 357: 539-545 (Feb. 2001).
Barclay, J.W. and Roberson,R.M., "Role for Calcium in Heat Shock-Mediated Synaptic Thermoprotection in *Drosophila* Larvae," *J. Neurobiol.*, 56(4): 360-371 (2003).
Beck, F-X., et al., "Molecular Chaperones in the Kidney: Distribution, Putative Roles, and Regulation,"*Am. J. Physiol. Renal. Physiol.*, 279: F203-F215 (2000).
Beillerot, et al., "Synthesis and protective effects of coumarin derivatives against oxidative stress induced by doxorubicin," Bioorganic & Medicinal Chemistry Letters, Oxford, GB, vol. 18, No. 3, Dec. 27, 2007, pp. 1102-1105, XP022475694, ISSN: 0960-894X.
Bellmann, K., et al., "Heat Shock Induces Resistance in Rat Pancreatic Islet Cells against Nitric Oxide, Oxygen Radicals and Streptozotocin Toxicity In Vitro," *J. Clin. Invest.*, 95(6): 2840-2845 (1995).
Berge, et al., "Pharmaceutical Salts," *J. Pharm. Sci.*, 66 (1): 1-19, 1977.
Biagi, G. et al., "1,5-Diarylsubstituted 1,2,3-triazoles as Potassium Channel Activators. VI," *Il Farmaco*, 59(5): 397-404 (2004), esp. p. 398.
Blondeau, N., et al., "Polyunsaturated Fatty Acids Induce Ischemic and Epileptic Tolerance," *Neuroscience*, 109(2): 231-241 (2002).
Calderwood S. R. et al,. "Extracellular Heat Schock Proteins in Cell Signaling and Immunity," *Annals of the New York Academy of Sciences*, 1113:28-29 (Oct. 2007).
Cancer, Wikipedia, http://en.wikipedia.org/wiki/Cancer (1 of 40) Aug. 2, 2008 (all pages).
Carmel, J.B., et al., "Mediators of Ischemic Preconditioning Identified by Microarray Analysis of Rat Spinal Cord," *Exp. Neurol.*, 185: 81-96 (2004).
Carter, R. J., et al., "Characterization of Progressive Motor Deficits in Mice Transgenic for the Human Huntington's Disease Mutation," *J. Neuroscience*, 19(8): 3248-3257 (1999).
Chen, H-C., et al., Induction of Heat Shock Protein 70 Protects Mesangial Cells Against Oxidative Injury, *Kidney Int.*, 56: 1270-1273 (1999).
Clathrate: Lewis, Hawley's Condensed Chemical Dictionary, 14th Edition, 1997, Van Nostrand Reinhold.
Craig, E. A., "The Heat Shock," *Crit. Rev. Biochem.*, 18(3): 239-280 (1985).
Daniels, G.A., et al., Nature Biotechnology, 22(9): 1125-1132 (Sep. 2004) (Epub Aug. 1, 2004).
Doi, Y., et al., "Effect of HSP70 Induced by Warm Ischemia to the Liver on Liver Function after Partial Hepatectomy," *Hepato-Gastroenterology*, 48: 533-540 (2001).

Dunn, S.E., et al., "Polystyrene-Poly (Ethylene Glycol) (PS-PEG2000) Particles as Model Systems for Site Specific Drug Delivery. 2. The Effect of PEG Surface Density on the in Vitro Cell Interaction and in Vivo Biodistribution," *Pharmaceutical Research* 11(7):1016-1022 (1994).
Dvorak, H.F., et al., "Identification and Characterization of the Blood Vessels of Solid Tumors That Are Leaky to Circulating Macromolecules," *American Journal of Pathology* 133(1):95-109 (1988).
Gabizon, A.A., "Selective Tumor Localization and Improved Therapeutic Index of Anthracyclines Encapsulated in Long-Circulating Liposomes," *Cancer Research* 52:891-896 (1992).
Gao, Y., et al., "Protein Kinase C-dependent Activation of P44/42 Mitogen-activated Protein Kinase and Heat Shock Protein 70 in Signal Transduction During Hepatocyte Ischemic Preconditioning," *World J. Gastroenterol.*, 10(7): 1019-1027 (2004).
Garlock, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.
Gavezzotti, "Are crystal structures predictable?," Accounts of Chemical Research, 27:309-314, 1994.
Gawande, N.G., et al., "Synthesis of some thiosemicarbazides and related compounds," CAPLUS, 1989, XP002391517.
Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.
Georgopoulos, C. and Welch, W. J., "Role of the Major Heat Shock Proteins as Molecular Chaperones,"*Annu. Rev. Cell Biol.*, 9: 601-634 (1993).
Golub et al., "Molecular Classification of Cancer: Class Discovery and Class Prediction by Gene Expression Monitoring," *Science*, vol. 286, 1999, pp. 531-537.
Goodman & Gilman's, The Pharmacological Basis of Therapeutics, Ninth Edition, (1996), Section X, Calabresi et al., pp. 1225-1232.
Gref, R., et al., "Biodegradable Long-Circulating Polymeric Nanospheres," *Science* 263:1600-1603 (1994).
Gura et al., "Systems for Identifying New Drugs are Often Faulty," *Science*, 1997, 278: 1041-1042.
Gurney, M. E., et al., "Motor Neuron Degeneration in Mice That Express a Human Cu,Zn Superoxide Dismutase Mutation," *Science*, 264: 1772-1775 (1994).
Hiratsuka, M., et al., "Heat Shock Pretreatment Protects Pulmonary Isografts from Subsequent Ischemia-reperfusion Injury," *J. Heart Lung Transplant*, 17(12): 1238-1246 (1998).
Hoffman, Henry, "Chemoradiotherapy: Emerging Treatment Improvement Strategies," *Head & Neck*, Feb. 2003, and published online in *Wiley InterScience* Dec. 6, 2003 (www.interscience.wiley.com).
Holcomb, L., et al., "Accelerated Alzheimer-Type phenotype in transgenic mice carrying both mutant *amyloid precursor protein* and *presenilin 1* transgenes," *Nature Medicine*, 4(1): 97-100 (1998).
Howland, D. S., et al., "Focal Loss of the Glutamate Transporter Eaat2 in a Transgenetic Rat Model of Sod1 Mutant-mediated Amyotrophic Lateral Sclerosis (ALS)," *Proc. Nat. Acad. Sci. USA*, 99(3): 1604-1609 (2002).
Ichihara, et al., "Roles of oxidative stress and Akt signaling in doxorubicin cardiotoxicity," *Biochemical and Biophysical Research Communications*, Academic Press Inc., Orlando, FL, US, vol. 359, No. 1, Jun. 2, 2007, pp. 27-33, XP022103137, ISSN: 0006-291X.
Inclusion complex: Lewis, Hawley's Condensed Chemical Dictionary, 14th Edition, 1997, Van Nostrand Reinhold.
Ishii, Y., et al., "Retinal Ganglion Cell Protection with Geranylgeranylacetone, a Heat Shock Protein Inducer, in a Rat Glaucoma Model," *Invest. Opthalmol. Vis. Sci.*, 44(5): 1982-1992 (2003).
Jacquier-Sarlin, M.R. et al., "Protective Effects of hsp70 in Inflammation," *Experientia*, 50(11-12): 1031-1038 (Nov. 1994).
Johnson et al., "Relationships Between Drug Activity in NCl Preclinical in vitro and in vivo Models and Early Clinical Trials," *British J. of Cancer*, 2001, 84(10): 1424-1431.
Johnson, A.D., et al., "Differential Distribution of 70-kD Heat Shock Protein Atherosclerosis," *Arterio Thromb Vasc Biol*, 15(1): 27-36 (1995).

Kandror, O. and Goldberg, A.L., "Trigger Factor is Induced Upon Cold Shock and Enhances Viability of *Escherichia coli* at Low Temperatures," *Proc Natl Acad Sci USA*, 94(10): 4978-4981 (1997).

Lee, J.E., et al., "Differential Neuroprotection From Human Heat Shock Protein 70 Overexpression in in Vitro and in Vivo Models of Ischemia and Ischemia-Like Conditions,"*Exp Neurol*, 170(1): 129-139 (2001).

Mosser, D.D., et al., "The Chaperone Function of hsp70 Is Required for Protecti Induced Apoptosis," *Mol Cell Biol*, 20(19): 7146-7159 (2000).

Papahadjopoulos, D., et al., "Sterically Stabilized Liposomes: Improvements in Pharmacokinetics and Antitumor Therapeutic Efficacy," *Proc. Natl. Acad. Sci. USA* 88:11460-11464 (1991).

Patani, et al., "Bioisosterism: A Rational Approach in Drug Design," Chem. Rev., 96: 3147-3176 (1996), esp. p. 3152.

Plumier, J.-C. L., et al., "Transgenic Mice Expressing the Human Heat Shock Protein 70 Have I proved Post-Ischemic Myocardial Recovery," *J Clin Invest*, 95: 1854-1860 (1995).

Radford, N.B., et al., "Cardioprotective Effects of 70-kDa Heat Shock Proteiin in Transgenic Mice," *Proc Natl Acad Sci USA*, 93(6): 2339-2342 (1996).

Renshaw, G.M.C., et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Sanchez, et al., "New naphthylcombretastatins. Modifications on the ethylene bridge," Bioorganic and Medicinal Chemistry, vol. 13, No. 6, Mar. 2005, pp. 2097-2107, XP002470852, ISSN: 0968-0896.

Sato, K., et al., "HSP70 is Essential to the Neuroprotective Effect of Heat-Shock," *Brain Res*, 740(1-2): 117-123 (1996).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Sausville et al., "Contributions to Human Tumor Xenografts to Anticancer Drug Development," *Cancer Research*, 2006, vol. 66, pp. 3351-3354.

Savage, E., et al., Living with Melanoma, [online], [retrieved on Aug. 9, 2006]. Retrieved from the Internet URL: http://ericandfran.com/melanona.htm.

Shin, K.D., et al., "Blocking tumor cell migration and invasion with biphenyl isoxazole derivative KRIBB3, a synthetic molecule that inhibits Hsp27 phosphorylation" *Journal of Biological Chemistry, American Society of Biochemical Biologists*, Birmingham, US, vol. 280 No. 50, Oct. 18, 2005, pp. 41439-41448, XP002391924, ISN: 0021-9258.

Simon, M.M., et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (In Japanese) English abstract, *Nihon Shinkei Seishin Yakurigaku Zasshi*, 21(1): 21-25 (2001).

Tanaka S., et al, "activation of T cells Recognizing an Epitipe of Heat-shock Protein 70 can protect against Rat Adjuvant Arthritis," *J. of Immunology* 163(10): 5560-5565 (1999).

Tavaria, M. et al., "A Hitchhiker's Guide to the Human Hsp70 Family," *Cell Stress Chaperones*, 1(1): 23-28 (1996).

Todryk, S.M., et al. "Facets of Heat Shock Protein 70 Show Immunotherapeutic Potential,", *Immunology*, 110(1): 1-9 (2003).

Tsuchiya, D., et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1188 (2003).

Valeriote, F., et al. "Synergistic Interaction of Anticancer Agents: A Cellular Perspective," *Cancer Chemotherapy Reports.*,59(5): 895-900 (1975).

Vippagunta, et al., "Crystalline solids," *Advanced Drug Delivery Reviews*, 48: 3-26, 2001.

Vleminckx, V., et al., "Upregulation of HSP27 in a Transgenic Model of ALS," *J Neuropathol Exp Neurol*, 61(11): 968-974 (2002).

Voss, R.M., et al., "Gender Differences in the Expression of Heat Shock Proteins: The Effect of Estrogen," *Am J Physiol Heart Circ Physiol*, 285: H687-H692 (2003).

Weichert et al., Taxol in malignant melanoma, J. Natl. Cancer Inst. monogr. 15:185-7 (1993 (abstract only).

Wust, P. et al., "Hyperthermia in Combined Treatment of Cancer," *The Lancet Oncology*, 3(8): 487-497 (Aug. 2002), XP004813895.

Yenari, M.A., "Heat Shock Proteins and Neuroprotection," *Adv Exp Med Biol*, 513: 281-299 (2002).

Yu, Q., et al., "Retinal Uptake of Intravitreally Injected Hsc/Hsp70 and its Effect on Susceptibility to Light Damage," *Molecular Vision*, 7: 48-56 (2001).

Zhang, Y., et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

* cited by examiner

Fig 2. Average % Body Weight Change

PACLITAXEL ENHANCER COMPOUND

RELATED APPLICATIONS

This application is a divisional application of U.S. patent application Ser. No. 11/244,427 (now U.S. Pat. No. 7,368,473, issued May 6, 2008), filed Oct. 5, 2005, which is a continuation of U.S. patent application Ser. No. 10/803,798 (now U.S. Pat. No. 7,001,923, issued Feb. 21, 2006), filed Mar. 18, 2004, which is a continuation of U.S. patent application Ser. No. 10/193,639 (now U.S. Pat. No. 6,762,204, issued Jul. 13, 2004), filed Jul. 10, 2002, which claims the benefit of U.S. Provisional Application No. 60/304,252, filed Jul. 10, 2001, and U.S. Provisional Application Ser. No. 60/361,936, filed Mar. 6, 2002. The entire teachings of these five applications are incorporated herein by reference.

BACKGROUND OF THE INVENTION

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

One serious limitation of combination chemotherapy is that anti-cancer agents generally have severe side effects, even when administered individually. For example, the well known anti-cancer agent paclitaxel causes neutroperia, neuropathy, mucositis, anemia, thrombocytopenia, bradycardia, diarrhea and nausea. Unfortunately, the toxicity of anti-cancer agents is generally additive when the drugs are administered in combination. As result, certain types of anti-cancer drugs are generally not combined. The combined toxic side-effects of those anti-cancer drugs that are administered simultaneously can place severe limitations on the quantities that can be used in combination. Often, it is not possible to use enough of the combination therapy to achieve the desired synergistic effects. Therefore, there is an urgent need for agents which can enhance the desirable tumor attacking properties of anti-cancer agents without further increasing their undesirable side-effects.

SUMMARY OF THE INVENTION

It has now been found that certain bis[thio-hydrazide amide] compounds significantly enhance the anti-cancer activity of paclitaxel. For example, Compound (1) was used in combination with paclitaxel (TAXOL) to treat tumors induced in nude mice from the human breast tumor cell line MDA-435. The tumor volume was about five fold less after 24 days of treatment in mice which had been administered 5 mg/kg of paclitaxel and 25 mg/kg of Compound (1) than in mice which had only been administered 5 mg/kg of paclitaxel or in mice which had only been administered 50 mg/kg of Compound (1) (Example 7). These results are shown graphically in FIG. 1. The structure of Compound (1) is shown below:

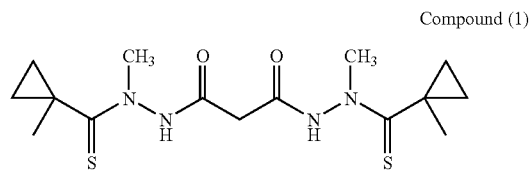

Compound (1)

It has also been found that these bis[thio-hydrazide amide] compounds have minimal toxic side effects. For example, the mice treated with paclitaxel and Compound (1) showed little if any weight loss over the treatment period (see FIG. 2). Based on these results, novel compounds which enhance the anti-cancer activity of paclitaxel, pharmaceutical compositions comprising these compounds and methods of treating a subject with cancer are disclosed herein.

One embodiment of the present invention is a compound represented by the Structural Formula (I):

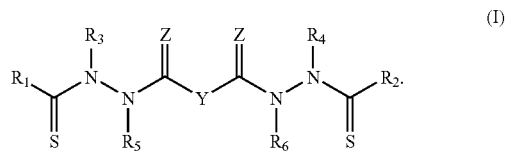

(I)

Y is a covalent bond, a phenylene group or a substituted or unsubstituted straight chained hydrocarbyl group. In addition, Y, taken together with both $>C=Z$ groups to which it is bonded, is a substituted or unsubstituted aromatic group. Preferably, Y is a covalent bond or $-C(R_7R_8)-$.

$R_1$ is an aliphatic group, a substituted aliphatic group, a non-aromatic heterocyclic group, or a substituted non-aromatic heterocyclic group.

$R_2$-$R_4$ are independently —H, an aliphatic group, a substituted aliphatic group, a non-aromatic heterocyclic group, a substituted non-aromatic heterocyclic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

$R_5$-$R_6$ are independently —H, an aliphatic group, a substituted aliphatic group, an aryl group or a substituted aryl group.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2-C6 substituted or unsubstituted alkylene group.

Z is $=O$ or $=S$.

In one aspect, $R_1$ and $R_2$ in the compound represented by Structural Formula (I) are not both C1-C5 alkyl (preferably not both methyl) when Y is $-C(R_7R_8)-$, $R_3$ and $R_4$ are both phenyl and $R_5$-$R_8$ are all —H.

Another embodiment of the present invention is a pharmaceutical composition comprising a pharmaceutically acceptable carrier or diluent and a compound represented by Structural Formula (I). Preferably, the pharmaceutical composition comprises an effective concentration of the compound.

Yet another embodiment of the present invention is a method of treating a subject with cancer. The method comprises administering to the subject an effective amount of paclitaxel or a paclitaxel analog and an effective amount of a compound represented by Structural Formula (I).

The disclosed compounds increase the anti-cancer activity of paclitaxel and paclitaxel analogs. In addition, these compounds have minimal toxic side-effects. Consequently, it is possible to increase the effectiveness of paclitaxel and analogs thereof when used in combination with the disclosed compounds, even when approaching the highest tolerated doses of paclitaxel. Thus, it is expected that combination therapy with the compounds of the present invention will provide improved clinical outcomes for patients with cancers that are being treated with paclitaxel. By co-administering the disclosed compounds with paclitaxel, it is also possible to achieve the same therapeutic effectiveness previously achieved with higher doses of paclitaxel, thereby reducing the side-effects and improving the quality of life for the patient.

DETAILED DESCRIPTION OF THE INVENTION

Figure 1:
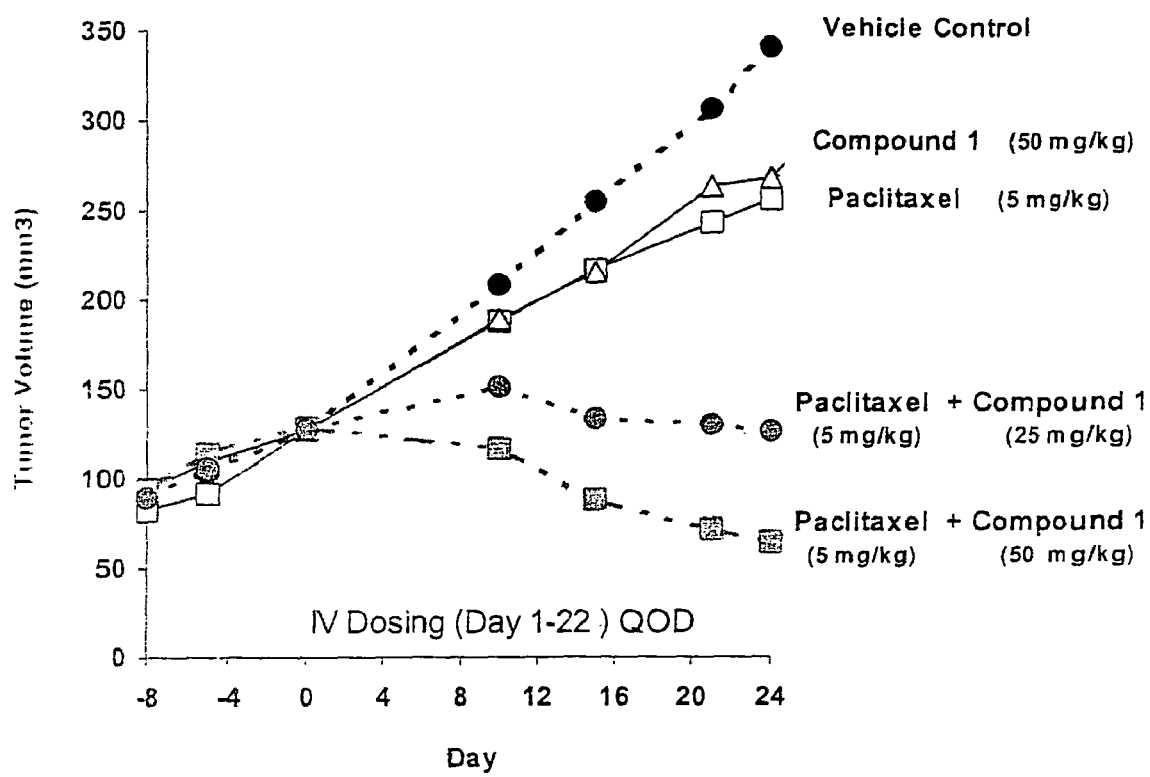
FIG. 1 is a graph showing the average tumor volume in milliliters over time (in days) in nude mice treated with vehicle (●); Compound (1) (25 mg/kg) (◆); Paclitaxel (15 mg/kg) (■); or Compound (1) (25 mg/kg) and Paclitaxel (15 mg/kg) (□). The tumors were generated from the human breast tumor cell line MDA-435.

The present invention is directed to compounds represented by Structural Formula (I) and the use thereof as paclitaxel enhancers in the treatment of cancer. In aspect, Y is a covalent bond or a substituted or unsubstituted straight chained hydrocarbyl group. In addition, Y, taken together with both >C=Z groups to which it is bonded, is a substituted or unsubstituted aromatic group (preferably, a covalent bond or —C($R_7R_8$)—); and $R_1$ is an aliphatic group or a substituted aliphatic group, $R_2$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. The remainder of the variables in Structural Formula (I) are as described above.

In a first preferred embodiment, Y in Structural Formula (I), taken together with both >C=Z groups to which it is bonded, is a substituted or unsubstituted arylene group and the compound is represented by Structural Formula (II):

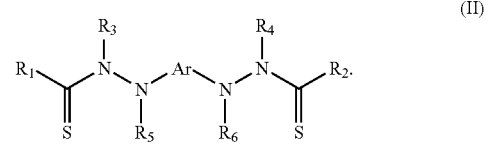

$R_1$-$R_6$ in Structural Formula (II) are as described in Structural Formula (I). Ar is a substituted or unsubstituted arylene group. Preferably, Ar is a nitrogen-containing heteroarylene group. Examples are shown below:

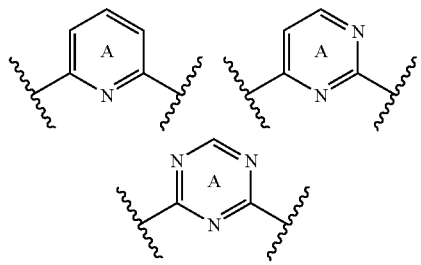

Ring A is substituted or unsubstituted.

In a second preferred embodiment, Y in Structural Formula (I) is a covalent bond or a substituted or unsubstituted straight chained hydrocarbyl group. $R_7$ and $R_8$ are as described for Structural Formula (I). Preferably, Y is a covalent bond, —C($R_7R_8$)—, —(CH$_2$CH$_2$)—, trans-(CH=CH)—, cis-(CH=CH)—, —(CC)— or a 1,4-phenylene group. Even more preferably, Y is a covalent bond or —C($R_7R_8$)—.

In a third preferred embodiment, Y in Structural Formula (I) is a covalent bond or —C($R_7R_8$)— and the compound of the present invention is represented by Structural Formula (III):

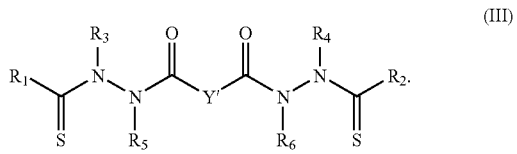

$R_1$-$R_8$ are as described for Structural Formula (I). Y' is a covalent bond or —C($R_7R_8$)—. Preferably, $R_7$ and $R_8$ are both methyl; $R_7$ and $R_8$, taken together, are propylene or butylene; or $R_7$ is —H and $R_8$ is lower alkyl (preferably methyl), thienyl, phenyl or benzyl.

In one example of a compound represented by Structural Formula (III), at least one of $R_1$-$R_2$ is a substituted aliphatic group, an unsubstituted aliphatic group, a substituted non-aromatic heterocyclic group or an unsubstituted non-aromatic heterocyclic group. Preferably, $R_5$-$R_8$ are all —H. In another example of a compound represented by Structural Formula (III), at least one of $R_1$-$R_2$ is an unsubstituted cyclic aliphatic group, a substituted cyclic aliphatic group, a substituted straight chained or branched aliphatic group, a substituted non-aromatic heterocyclic group, or an unsubstituted non-aromatic heterocyclic group. In these two examples, $R_3$ and $R_4$ are preferably methyl.

In a more preferred embodiment, $R_5$-$R_8$ in Structural Formula (III) are —H and the compound is represented by Structural Formula (IV):

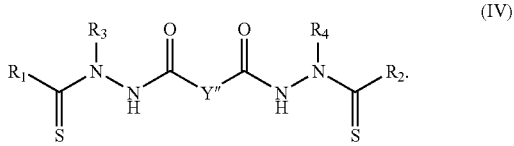

$R_1$-$R_4$ in Structural Formula (IV) are as described in Structural Formula (I). Y" is a covalent bond or —CH$_2$—.

In a first example of a compound represented by Structural Formula (IV), $R_3$ and $R_4$ are both a substituted or unsubstituted aliphatic group, preferably both a substituted or unsubstituted lower alkyl group and more preferably both a methyl group or ethyl. When $R_3$ and $R_4$ in Structural Formula (IV) are both a substituted or unsubstituted aliphatic group, then: 1) $R_1$ and $R_2$ are preferably both a substituted or unsubstituted aliphatic group (preferably a substituted or unsubstituted alkyl group and more preferably a C3-C8 substituted or unsubstituted cyclic aliphatic group such as a substituted or unsubstituted cyclopropyl group); or 2) $R_1$ is preferably a substituted or unsubstituted aliphatic group (preferably a substituted or unsubstituted cyclic aliphatic group); and $R_2$ is preferably: i) a substituted or unsubstituted aryl group (e.g., a substituted or unsubstituted heteroaryl group or a substituted or unsubstituted phenyl group; or ii) an substituted or unsubstituted aliphatic group (preferably a substituted or unsubstituted C3-C8 cyclic aliphatic group).

In a second example of a compound represented by Structural Formula (IV), $R_3$ and $R_4$ are both a substituted or unsubstituted heteroaryl group. When $R_3$ and $R_4$ in Structural Formula (IV) are both a substituted or unsubstituted heteroaryl group, then: 1) $R_1$ and $R_2$ are preferably both a substituted or unsubstituted aliphatic group (preferably a substituted or unsubstituted alkyl group); or 2) $R_1$ is preferably a substituted or unsubstituted aliphatic group (preferably a substituted or unsubstituted C3-C8 cyclic aliphatic group); and $R_2$ is preferably: i) a substituted or unsubstituted aryl group (e.g., a substituted or unsubstituted heteroaryl group or a substituted or unsubstituted phenyl group; or ii) an substituted or unsubstituted aliphatic group (preferably a substituted or unsubstituted cyclic aliphatic group).

In a third example of a compound represented by Structural Formula (IV), $R_3$ and $R_4$ are both a substituted or unsubstituted phenyl group (e.g., a phenyl group substituted with at least one group other than an aliphatic group). When $R_3$ and $R_4$ in Structural Formula (IV) are both a substituted or unsubstituted phenyl group, then: 1) $R_1$ and $R_2$ are preferably both a substituted or unsubstituted aliphatic group (preferably a substituted or unsubstituted alkyl group and more preferably a C3-C8 substituted or unsubstituted cyclic aliphatic group such as a substituted or unsubstituted cyclopropyl group); or 2) $R_1$ is preferably a substituted or unsubstituted aliphatic group (preferably a substituted or unsubstituted cyclic aliphatic group); and $R_2$ is preferably: i) a substituted or unsubstituted aryl group (e.g., a substituted or unsubstituted heteroaryl group or a substituted or unsubstituted phenyl group; or ii) an substituted or unsubstituted aliphatic group (preferably a substituted or unsubstituted cyclic aliphatic group).

In a fourth example of a compound represented by Structural Formula (IV), $R_1$ and $R_2$ are both a substituted or unsubstituted aliphatic group, preferably both a substituted or unsubstituted lower alkyl group, including a C3-C8 cycloalkyl group substituted with at least one lower alkyl group (e.g., methyl, ethyl, n-propyl, n-butyl, n-pentyl, cyclopropyl, 1-methylcyclopropyl, 2-methylcyclopropyl, cyclobutyl, cyclopentyl, or cyclohexyl). When $R_1$ and $R_2$ in Structural Formula (IV) are both an aliphatic group or a substituted aliphatic group, then $R_3$ and $R_4$ are preferably both: 1) a substituted or unsubstituted aryl group (e.g., a substituted or unsubstituted heteroaryl group, a substituted or unsubstituted phenyl group, or a phenyl group with at least one substituent other than an aliphatic group); or 2) a substituted or unsubstituted aliphatic group (preferably a substituted or unsubstituted alkyl group).

In a fifth example of a compound represented by Structural Formula (IV), $R_1$ and $R_2$ are both a substituted or unsubstituted cyclic aliphatic group, preferably both a substituted or unsubstituted cyclopropyl alkyl group.

In a sixth example of a compound represented by Structural Formula (IV), $R_1$ is a substituted or unsubstituted aliphatic group and $R_2$ is a substituted or unsubstituted aryl group.

The following are specific examples of compounds represented by Structural Formula (IV): $R_1$ and $R_2$ are both methyl, and $R_3$ and $R_4$ are both p-CF$_3$-phenyl; $R_1$ and $R_2$ are both methyl, and $R_3$ and $R_4$ are both o-CH$_3$-phenyl; $R_1$ and $R_2$ are both —CH$_2$)$_3$COOH; and $R_3$ and $R_4$ are both phenyl; $R_1$ and $R_2$ are both represented by the following structural formula:

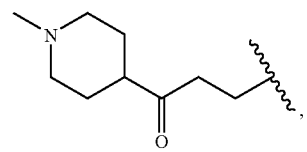

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

In a fourth preferred embodiment, Y in Structural Formula (I) is —C($R_7$R)— and $R_5$ and $R_6$ are both —H. When Y is a covalent bond or —CR$_7$R$_8$— and $R_5$ and $R_6$ are both —H, the compound of the present invention is represented by Structural Formula (V):

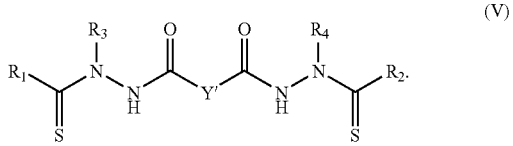

(V)

$R_1$-$R_4$, $R_7$ and $R_8$ are as described for Structural Formula (I) and Y' is a covalent bond or —$CR_7R_8$—. $R_7$ and $R_8$ are the same or different. Preferably, $R_7$ and $R_8$ are both methyl; $R_7$ and $R_8$, taken together, are propylene or butylene; or $R_7$ is —H and $R_8$ is lower alkyl (preferably methyl), thienyl, phenyl or benzyl.

In one example of a compound represented by Structural Formula (V), $R_1$ and $R_2$ are both a lower alkyl group or a substituted lower alkyl group and $R_3$ and $R_4$ are both an aryl group or a substituted aryl group. In another example of a compound represented by Structural Formula (V), $R_1$ and $R_2$ are both substituted or unsubstituted aliphatic groups and $R_3$ and $R_4$ are both a lower alkyl group or a substituted lower alkyl group; preferably, $R_1$ and $R_2$ are both substituted or unsubstituted alkyl groups (more preferably substituted or unsubstituted cyclic alkyl groups), $R_3$ and $R_4$ are both —H, methyl or ethyl, $R_7$ is —H and $R_8$ is —H or methyl. In yet another example of a compound represented by Structural Formula (V), $R_1$ and $R_2$ are both C3-C8 cyclic alkyl or substituted C3-C8 cyclic alkyl and $R_3$ and $R_4$ are both methyl, ethyl, phenyl, or thienyl (preferably, $R_7$ and $R_8$ are: 1) both methyl; 2) taken together, propylene or butylenes; or 3) $R_7$ is —H and $R_8$ is lower alkyl, thienyl, phenyl or benzyl). In yet another example of a compound represented by Structural Formula (V), $R_1$ and $R_2$ are both a lower alkyl group or a substituted lower alkyl group and $R_3$ and $R_4$ are both methyl, ethyl or phenyl.

The following are specific examples of compounds represented by Structural Formula (V): $R_1$ and $R_2$ are both cyclopropyl; $R_3$ and $R_4$ are both methyl; $R_7$ and $R_8$ are both —H; $R_1$ and $R_2$ are both cyclopropyl; $R_3$ and $R_4$ are both ethyl; $R_7$ and $R_8$ are both —H; $R_1$ and $R_2$ are both cyclopropyl; $R_3$ and $R_4$ are both methyl; $R_7$ is methyl; $R_8$ is —H; $R_1$ and $R_2$ are both 1-methylcyclopropyl; $R_3$ and $R_4$ are both methyl; Y' is bond; $R_1$ and $R_2$ are both 1-methylcyclopropyl; $R_3$ and $R_4$ are both methyl; $R_7$ and $R_8$ are both —H; $R_1$ and $R_2$ are both 1-methylcyclopropyl; $R_3$ and $R_4$ are both methyl; $R_7$ is methyl and $R_8$ is —H; $R_1$ and $R_2$ are both 1-methylcyclopropyl; $R_3$ and $R_4$ are both methyl; $R_7$ is ethyl and $R_8$ is —H; $R_1$ and $R_2$ are both 1-methylcyclopropyl; $R_3$ and $R_4$ are both methyl; $R_7$ is n-propyl and $R_8$ is —H; $R_1$ and $R_2$ are both 1-methylcyclopropyl; $R_3$ and $R_4$ are both methyl; $R_7$ and $R_8$ are both methyl; $R_1$ and $R_2$ are both 1-methylcyclopropyl; $R_3$ and $R_4$ are both ethyl; $R_7$ and $R_8$ are both —H; $R_1$ and $R_2$ are both 1-methylcyclopropyl; $R_3$ is methyl, and $R_4$ is ethyl; $R_7$ and $R_8$ are both —H; $R_1$ and $R_2$ are both 2-methylcyclopropyl; $R_3$ and $R_4$ are both methyl; $R_7$ and $R_8$ are both —H; $R_1$ and $R_2$ are both 2-phenylcyclopropyl; $R_3$ and $R_4$ are both methyl; $R_7$ and $R_8$ are both —H; $R_1$ and $R_2$ are both 1-phenylcyclopropyl; $R_3$ and $R_4$ are both methyl; $R_7$ and $R_8$ are both —H; $R_1$ and $R_2$ are both cyclobutyl; $R_3$ and $R_4$ are both methyl; $R_7$ and $R_8$ are both —H; $R_1$ and $R_2$ are both cyclopentyl; $R_3$ and $R_4$ are both methyl; $R_7$ and $R_8$ are both —H; $R_1$ and $R_2$ are both cyclohexyl; $R_3$ and $R_4$ are both methyl; $R_7$ and $R_8$ are both —H; $R_1$ and $R_2$ are both cyclohexyl; $R_3$ and $R_4$ are both phenyl; $R_7$ and $R_8$ are both —H; $R_1$ and $R_2$ are both methyl; $R_3$ and $R_4$ are both methyl; $R_7$ and $R_8$ are both methyl; $R_3$ and $R_4$ are both t-butyl; $R_7$ and $R_8$ are both —H; $R_1$ and $R_2$ are both methyl; $R_3$ and $R_4$ are both phenyl; $R_7$ and $R_8$ are both —H; $R_1$ and $R_2$ are both t-butyl; $R_3$ and $R_4$ are both methyl; $R_7$ and $R_8$ are both —H; $R_1$ and $R_2$ are ethyl; $R_3$ and $R_4$ are both methyl; $R_7$ and $R_8$ are both —H; $R_1$ and $R_2$ are both n-propyl; $R_3$ and $R_4$ are both methyl; $R_7$ and $R_8$ are both —H;

In a fifth preferred embodiment, Y in Structural Formula (I) is a covalent bond or —$CH_2$—. When Y is a covalent bond or —$CH_2$—, the compound of the present invention is represented by Structural Formula (VI):

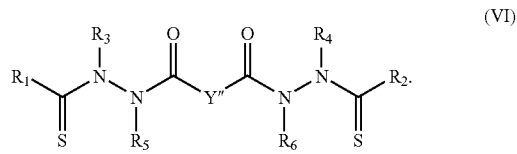

(VI)

$R_1$-$R_6$ in Structural Formula (VI) are as described for Structural Formula (I). $R_5$ and $R_6$ are the same or different. Y" is a covalent bond or —$CH_2$—.

In one example of a compound represented by Structural Formula (VI), $R_5$ and $R_6$ are both a lower alkyl group (preferably methyl) or a phenyl group. When $R_5$ and $R_6$ are both a lower alkyl group or a phenyl group, then $R_1$ and $R_2$ are preferably both lower alkyl or substituted lower alkyl and $R_3$ and $R_4$ are preferably both phenyl or substituted phenyl. Alternatively, when $R_5$ and $R_6$ are both a lower alkyl group or a phenyl group, $R_1$ and $R_2$ are both a lower alkyl group or a substituted lower alkyl group and $R_3$ and $R_4$ are both lower alkyl or substituted lower alkyl.

In Structural Formulas (I)-(VI), $R_1$ and $R_2$ are the same (e.g., $R_1$ and $R_2$ are both the same substituted or unsubstituted aliphatic group) or different (e.g., $R_1$ is a substituted or unsubstituted aliphatic group and $R_2$ is a substituted or unsubstituted aryl group); and/or $R_3$ and $R_4$ are the same or different. Preferably, $R_1$ and $R_2$ are the same, and $R_3$ and $R_4$ are the same.

A "straight chained hydrocarbyl group" is an alkylene group, i.e., —$(CH_2)_x$—, with one or more (preferably one) methylene groups optionally replaced with a linkage group. x is a positive integer (e.g., between 1 and about 10), preferably between 1 and about 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine [—N($R^a$)]—, wherein $R^a$ is defined below. A preferred linkage group is —C($R_7R_8$)—, wherein $R_7$ and $R_8$ are defined above. Suitable substituents for an alkylene group and a hydrocarbaryl group are those which do not substantially interfere with the reactions described herein. $R_7$ and $R_8$ are preferred substituents for an alkylene or hydrocarbyl group.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms, e.g., cyclopropyl, clobutyl, cyclopentyl, cyclohexyl, or cyclooctyl. A C1-C20 straight chained or branched alkyl group or a C3-C8 cyclic alkyl group is also referred to as a "lower alkyl" group.

Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

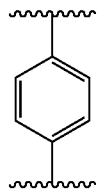

Substituents for an arylene group are as described below for an aryl group.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

The terms "lower alkoxy", "lower acyl", "(lower alkoxy)methyl" and "(lower alkyl)thiomethyl" mean to —O-(lower alkyl), —C(O)-(lower alkyl), —CH$_2$—O-(lower alkyl) and —CH$_2$—S-(lower alkyl), respectively. The terms "substituted lower alkoxy" and "substituted lower acyl" mean —O-(substituted lower alkyl) and —C(O)-(substituted lower alkyl), respectively.

Suitable substituents on an aliphatic group, non-aromatic heterocyclic group. benzylic or aryl group (carbocyclic and heteroaryl) are those which do not substantially interfere with the ability of the disclosed compounds to enhance the anti-cancer activity of paclitaxel and analogs thereof. A substituent substantially interferes with the ability of a disclosed compound to enhance anti-cancer activity when the enhancement is reduced by more than about 50% in a compound with the substituent compared with a compound without the substituent. Examples of suitable substituents include —OH, halogen (—Br, —Cl, —I and —F), —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SO$_k$R$^a$ (k is 0, 1 or 2) and —NH—C(=NH)—NH$_2$. R$^a$-R$^d$ are each independently an aliphatic, substituted aliphatic, benzyl, substituted benzyl, aromatic or substituted aromatic group, preferably an alkyl, benzylic or aryl group. In addition, —N(R$^a$R$^b$), taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Also included in the present invention are pharmaceutically acceptable salts of the compounds described herein. The compound of the present invention which possess a sufficiently acidic, a sufficiently basic, or both functional groups, and accordingly can react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Figure 4:
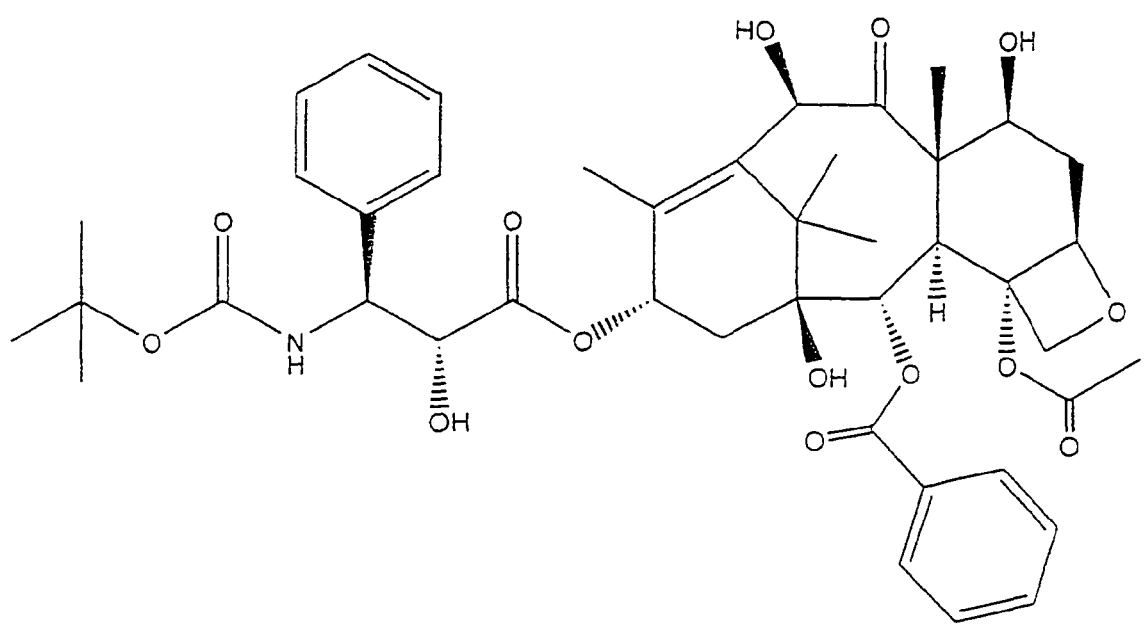
FIG. 4 is the structure of Docetaxel (TAXOTERE)
Figure 5:
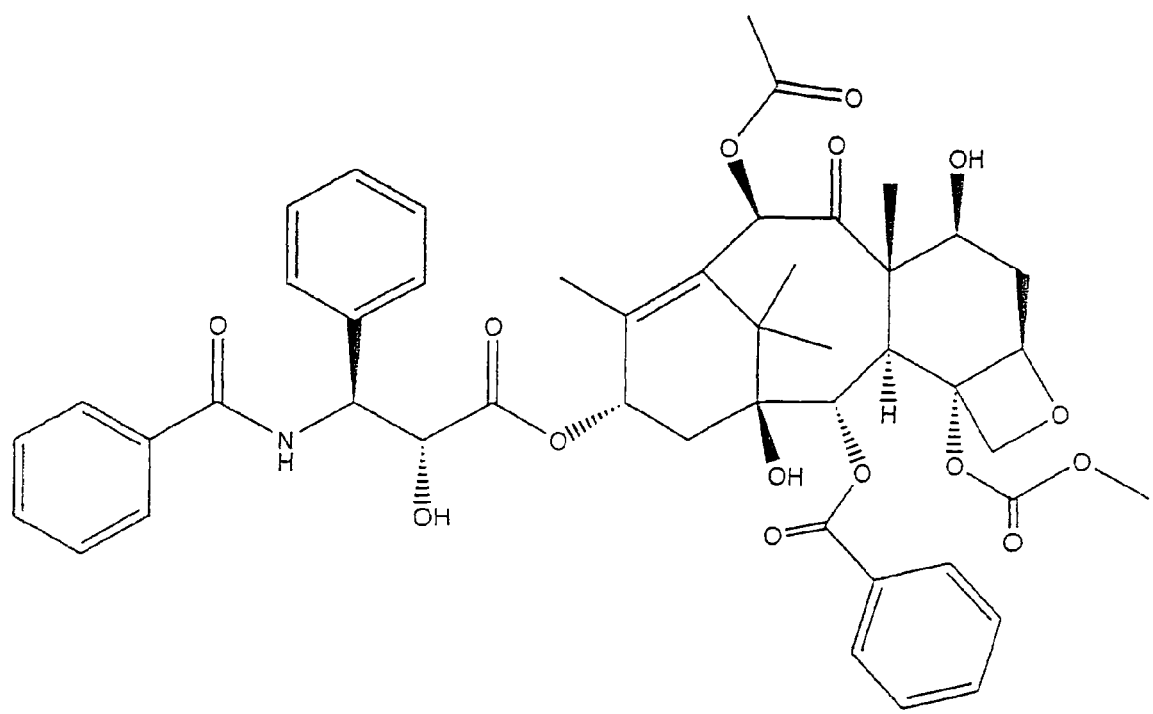
FIGS. 5-25 are each the structure of a paclitaxel analog.
Figure 6:
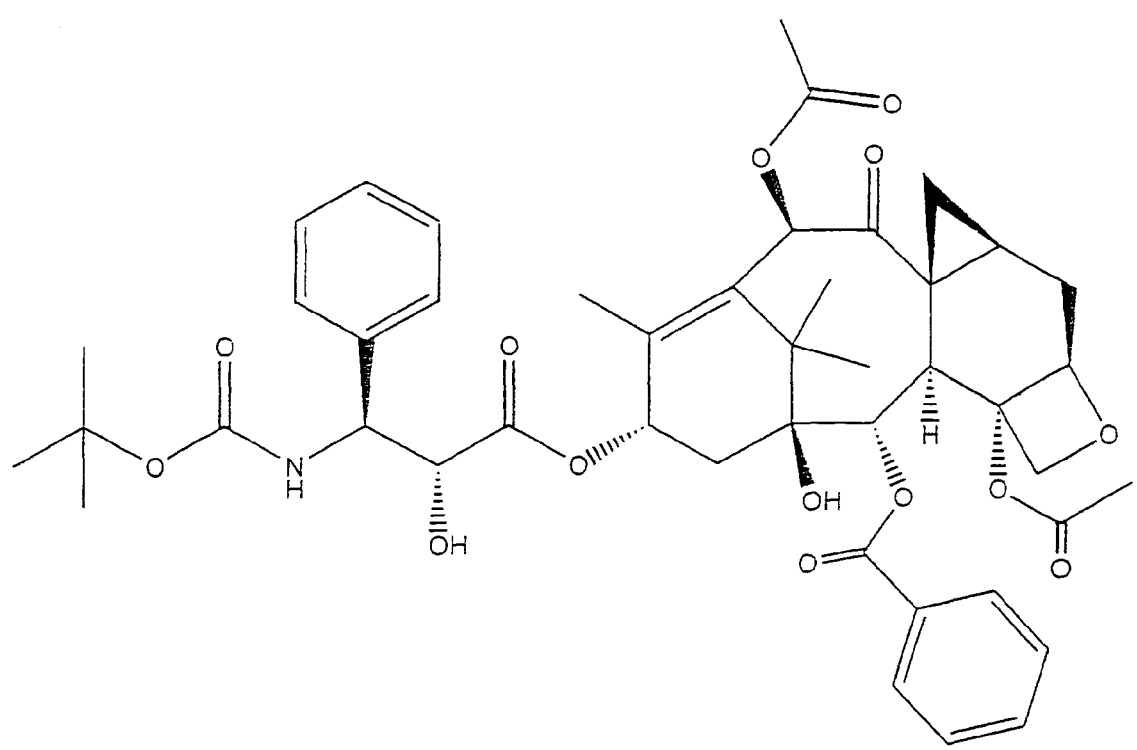
Figure 7:
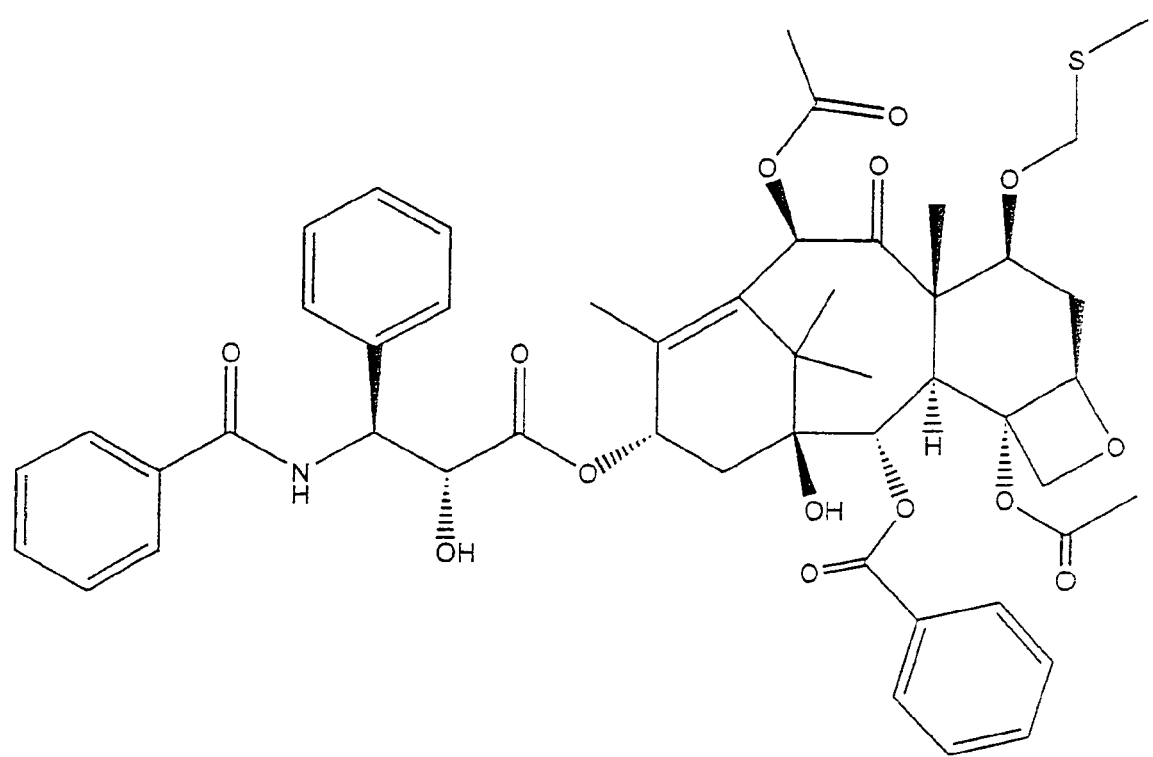
Figure 8:
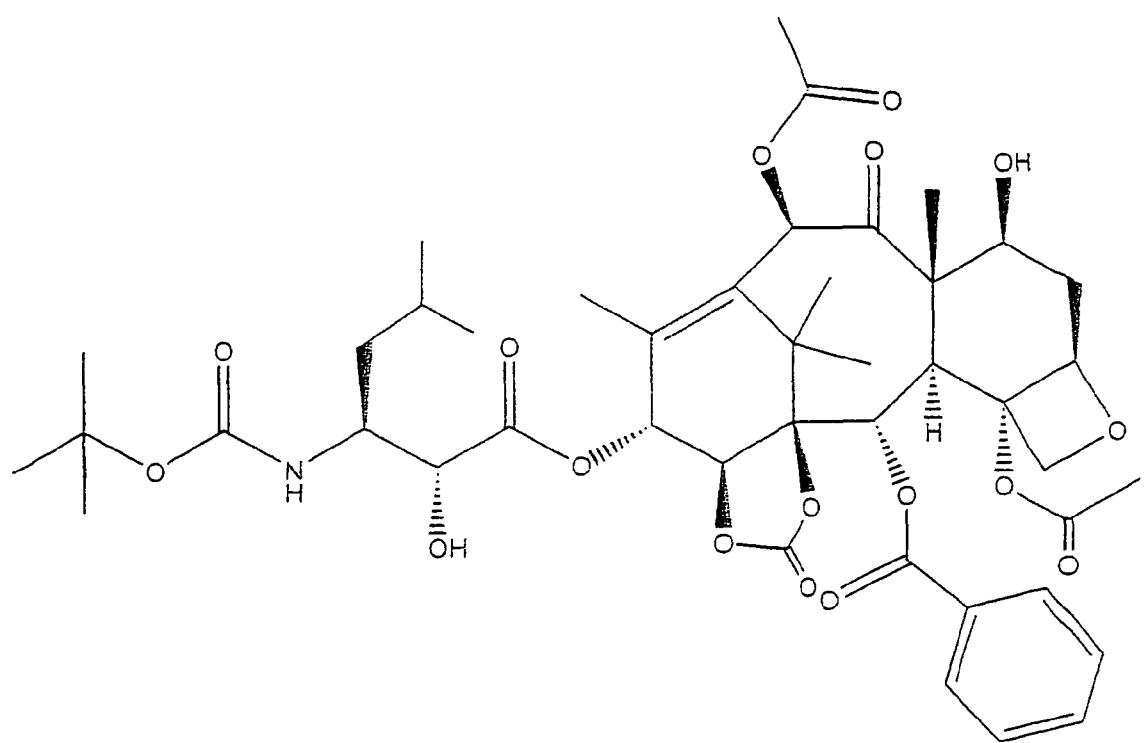
Figure 9:
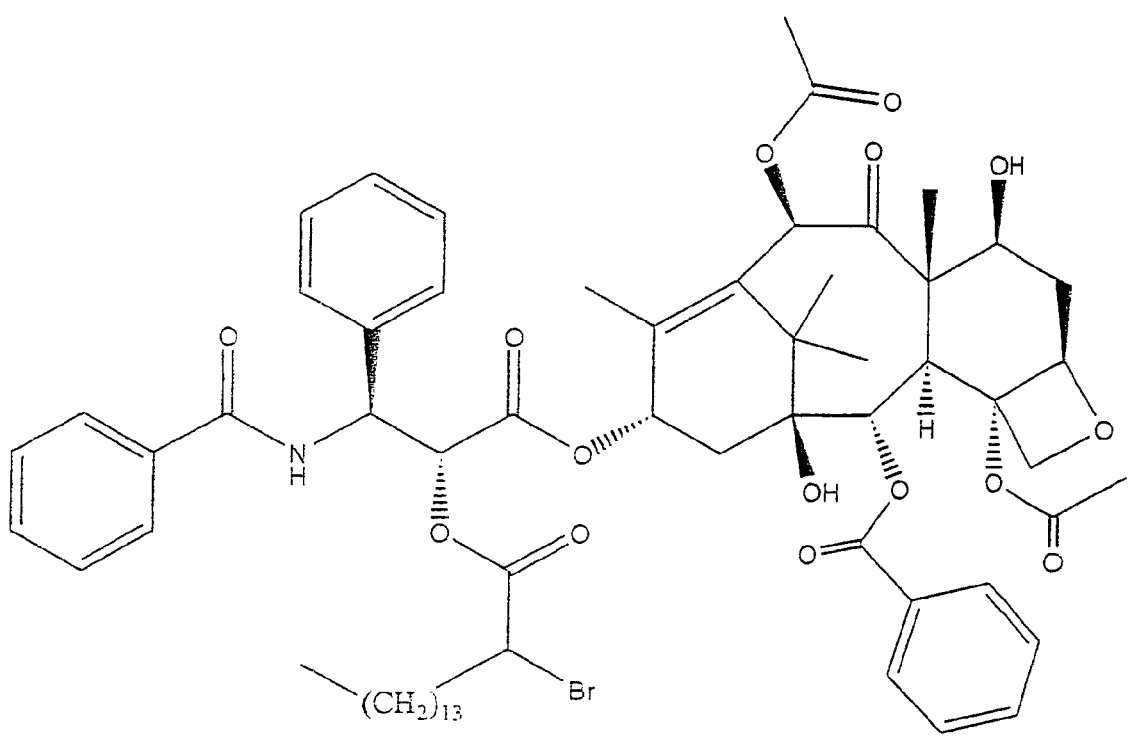
Figure 10:
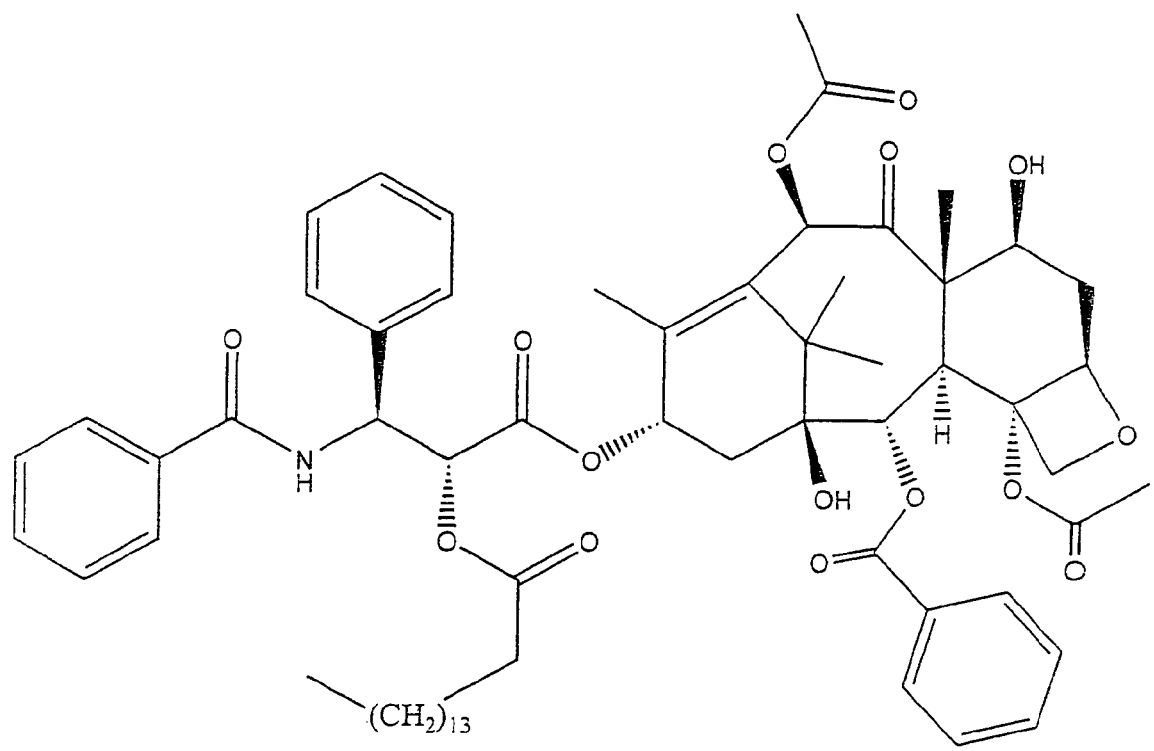
Figure 11:
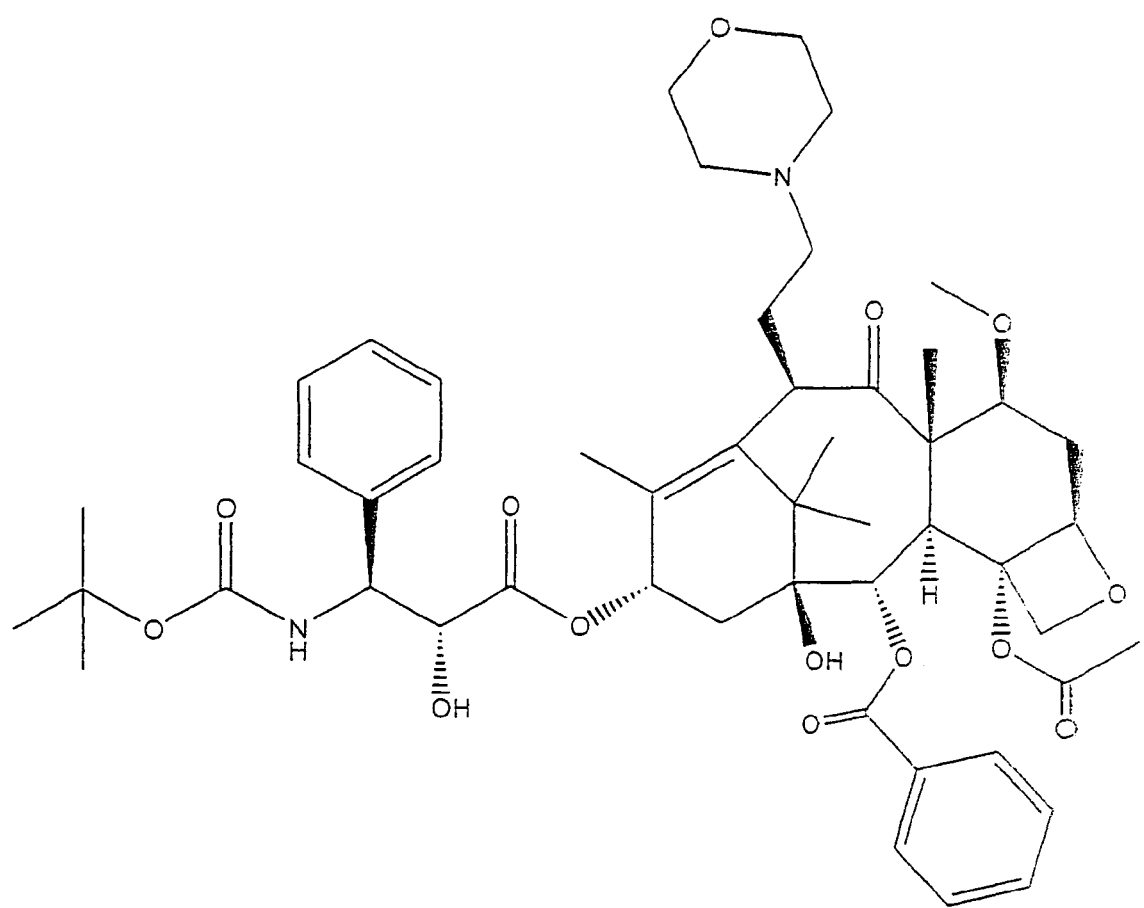
Figure 12:
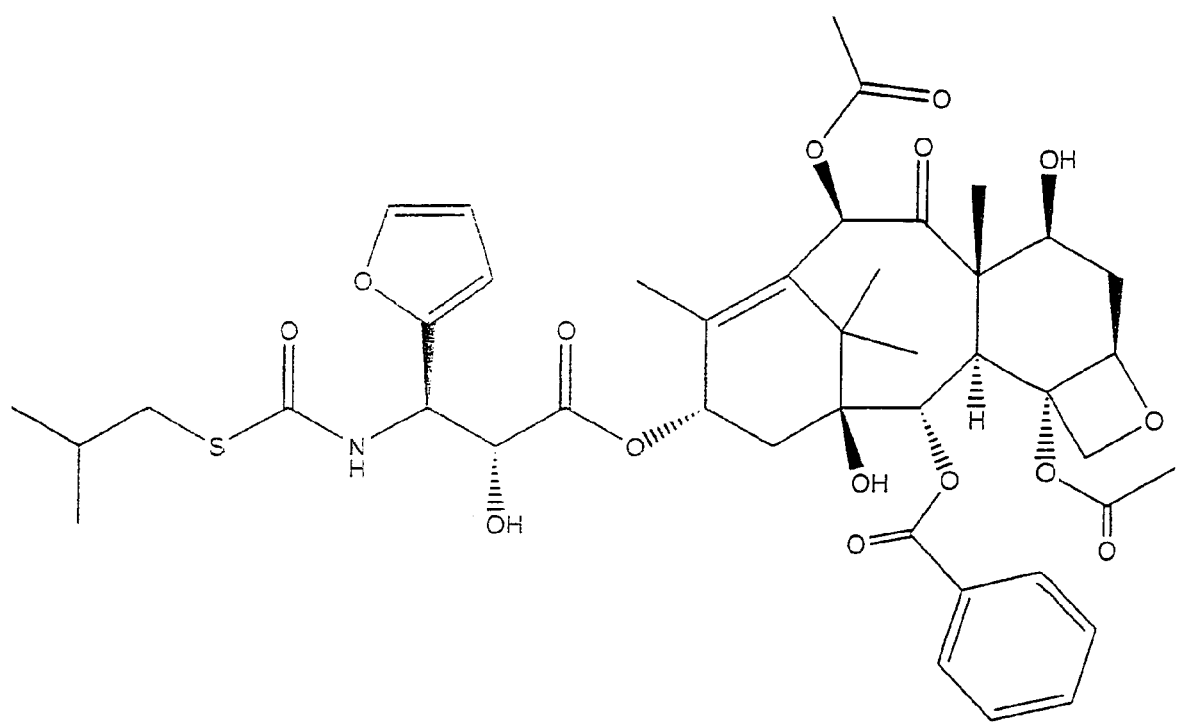
Figure 13:
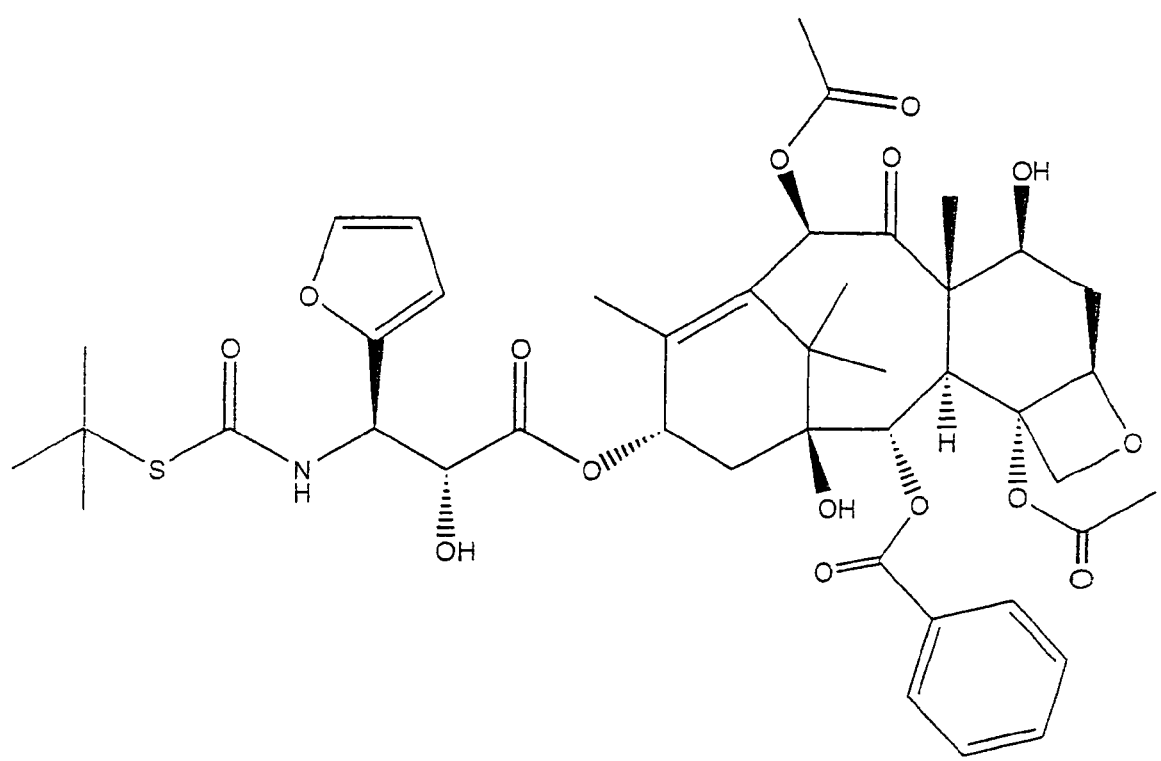
Figure 14:
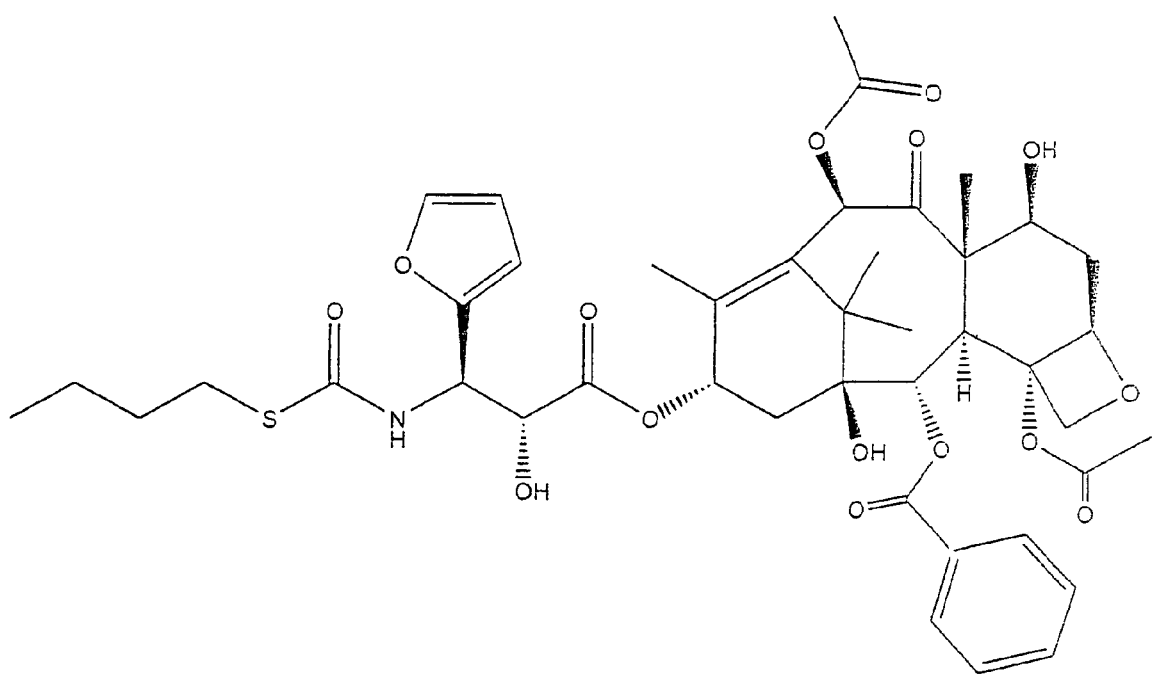
Figure 15:
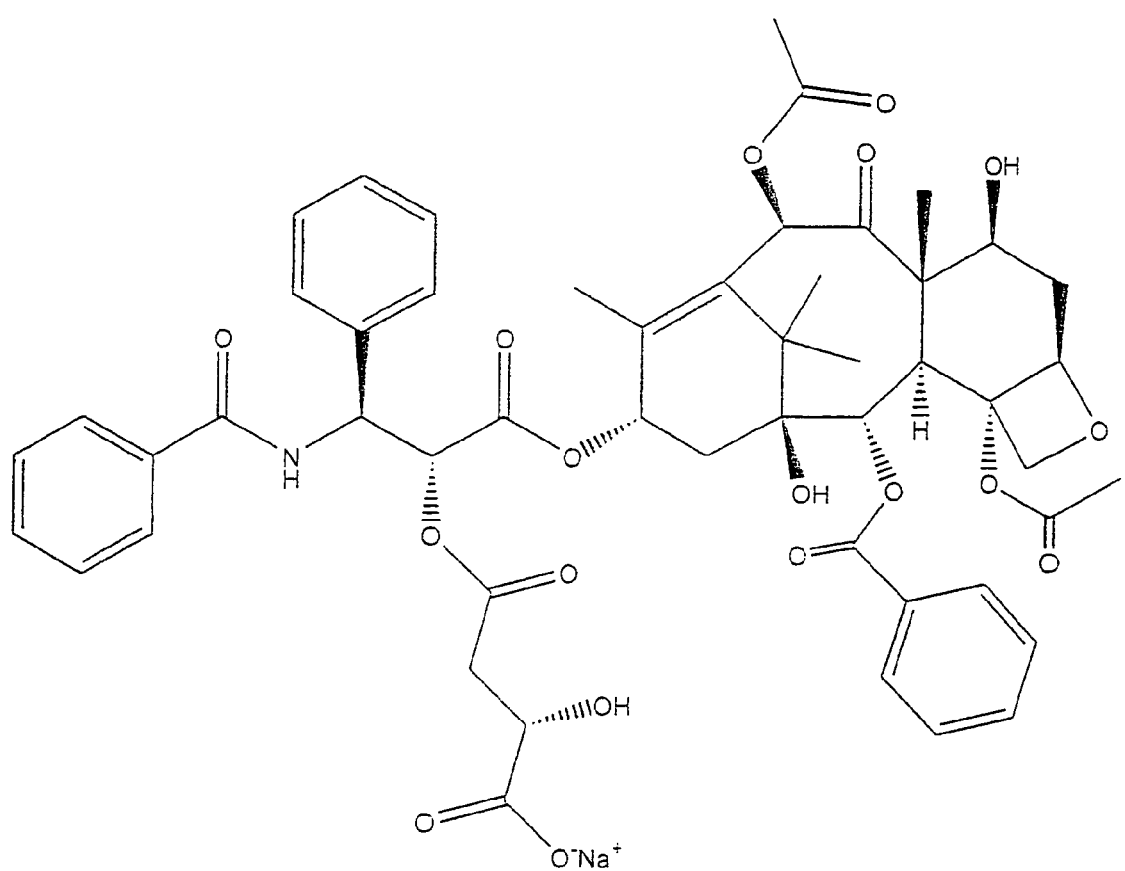
Figure 16:
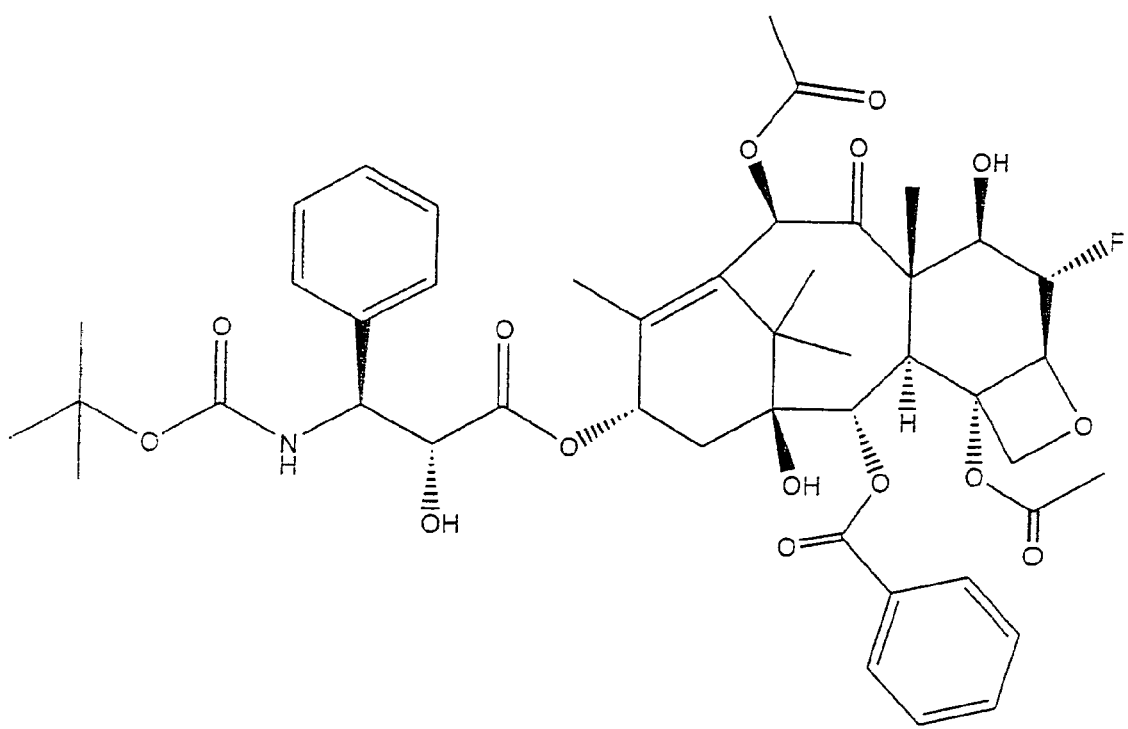
Figure 17:
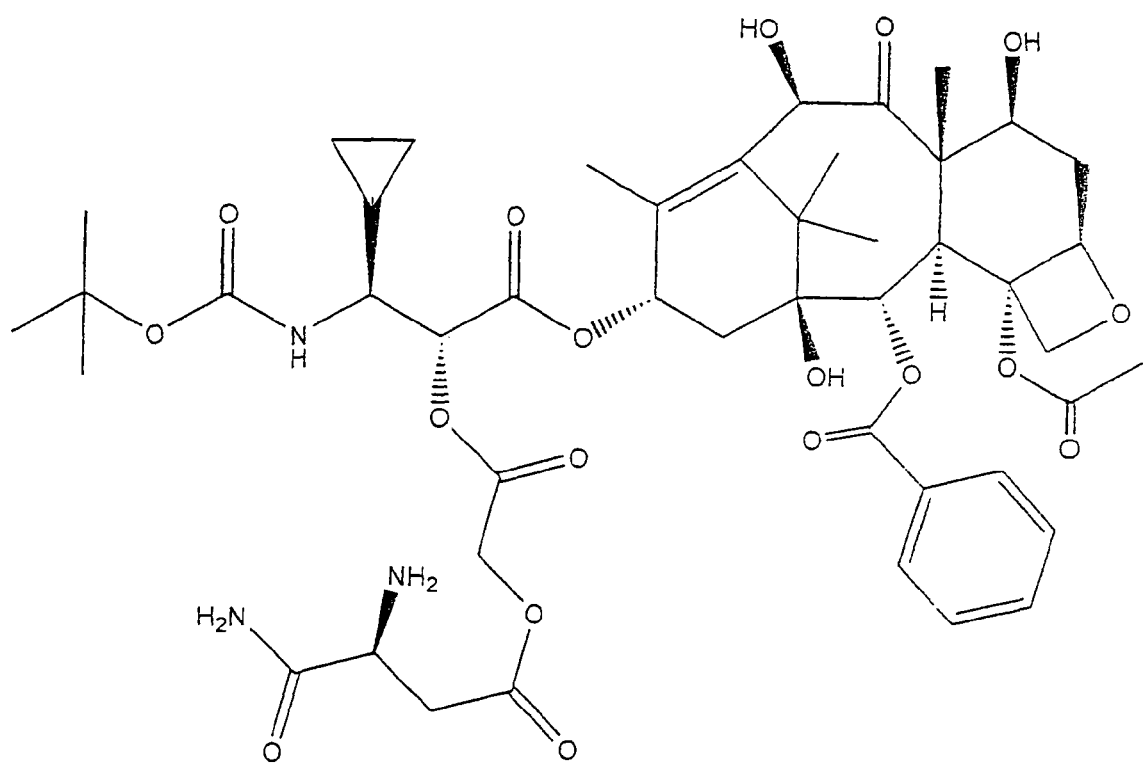
Figure 18:
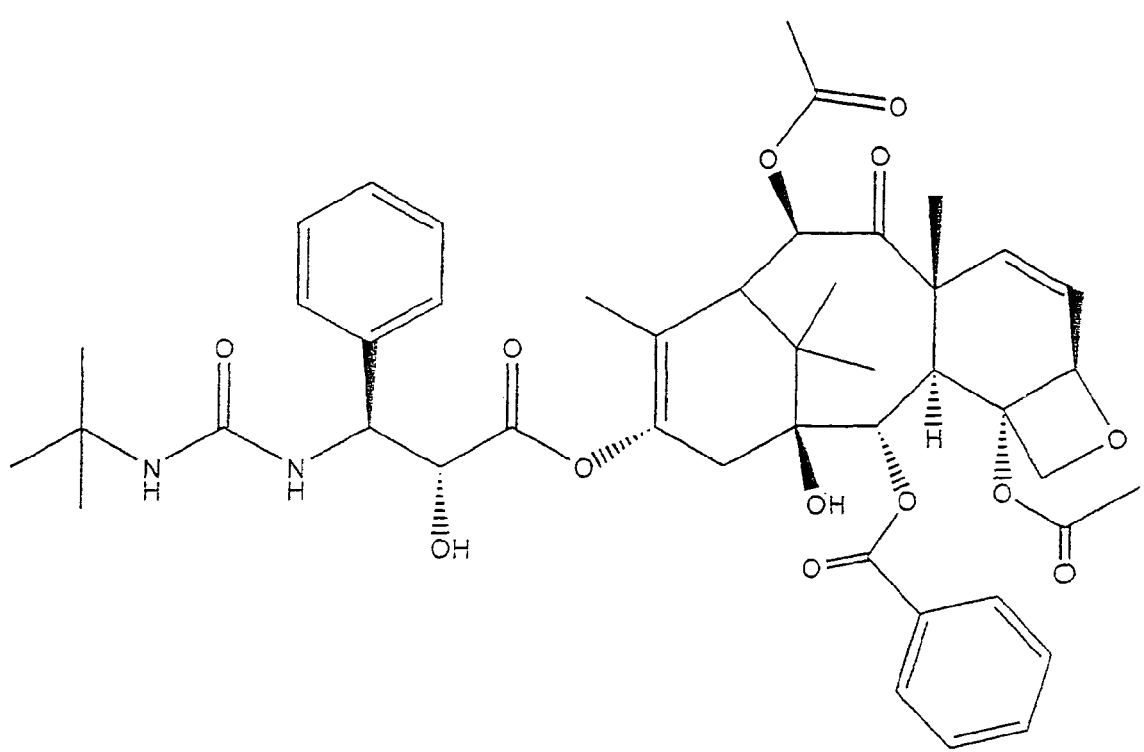
Figure 19:
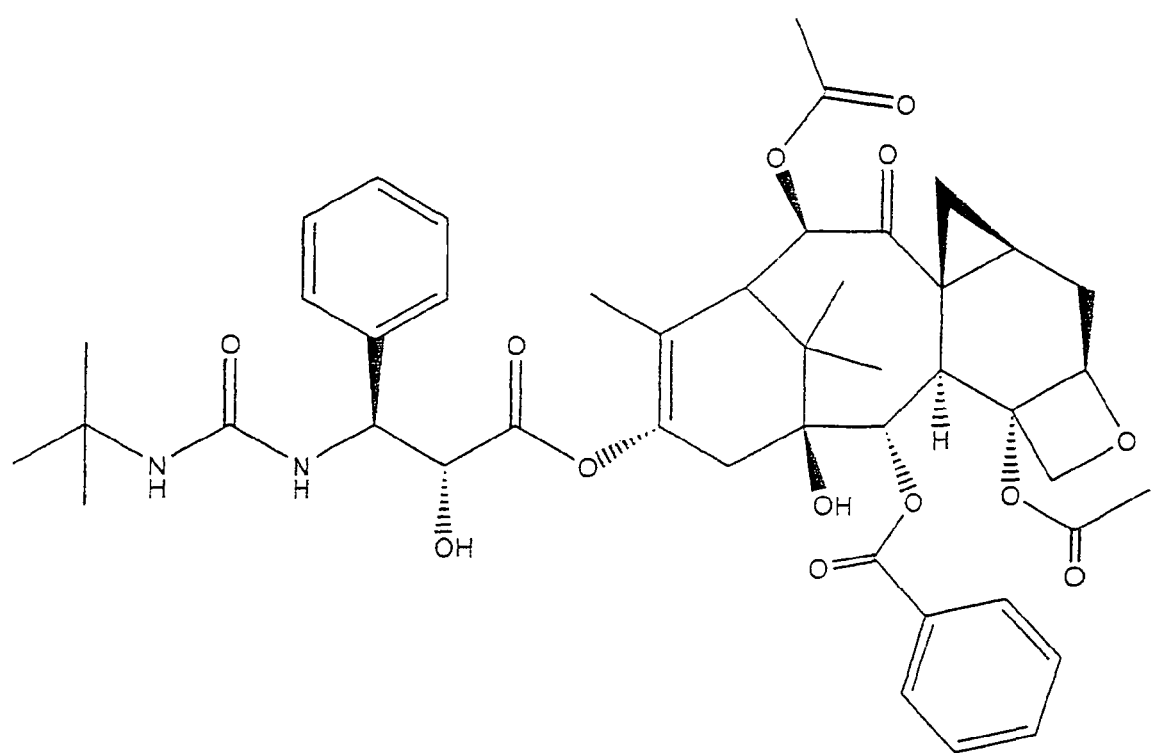
Figure 20:
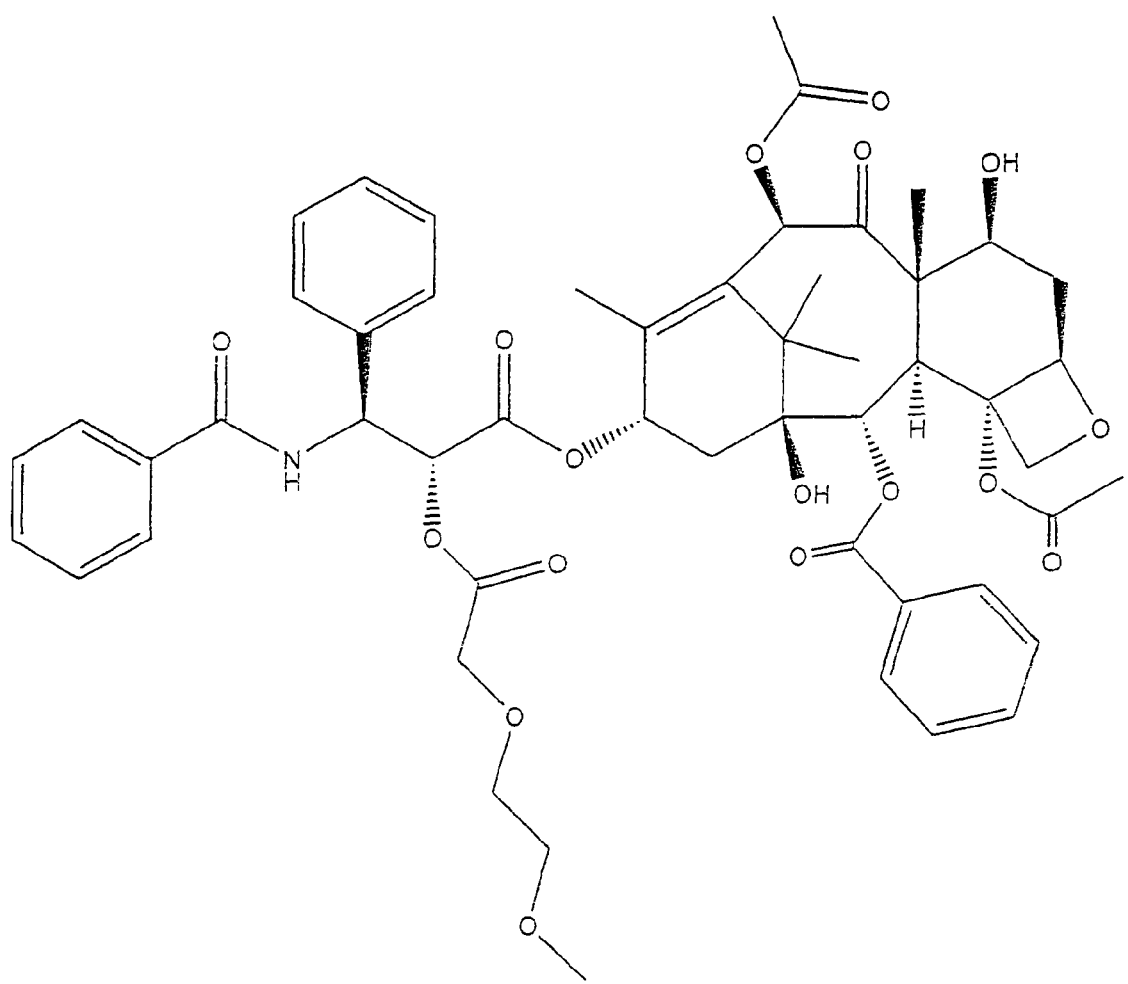
Figure 21:
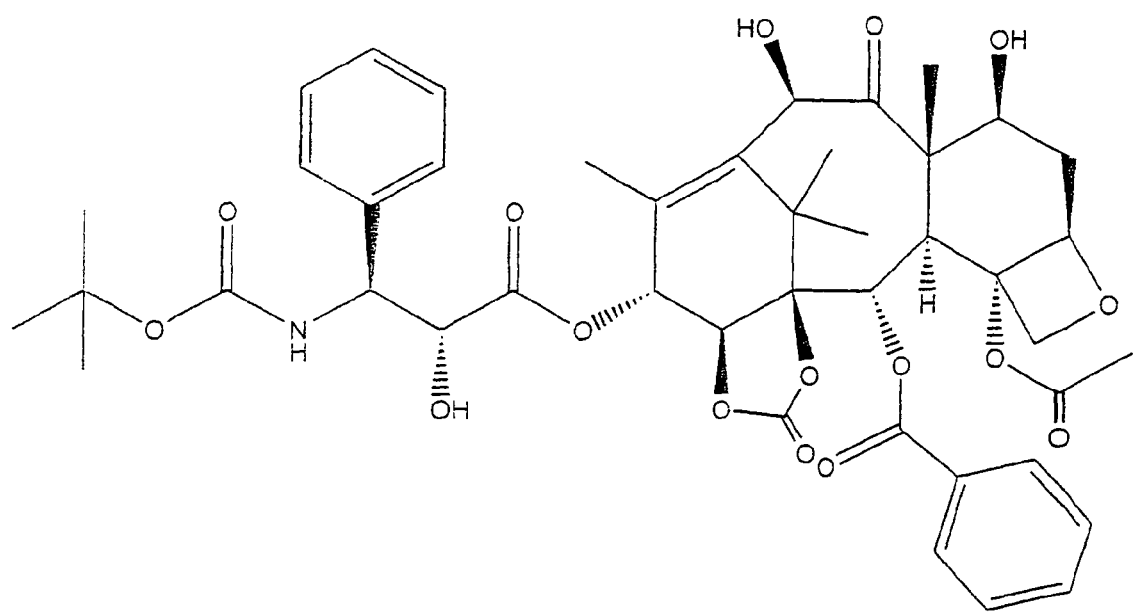
Figure 22:
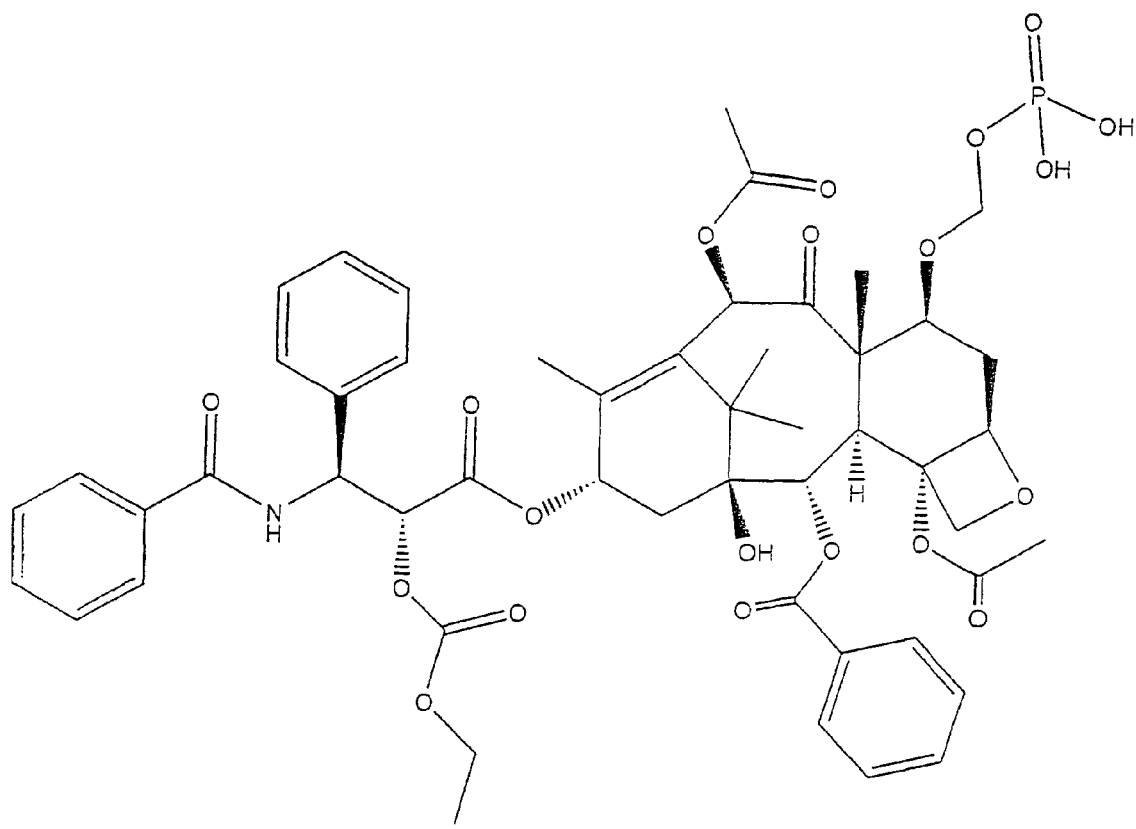
Figure 23:
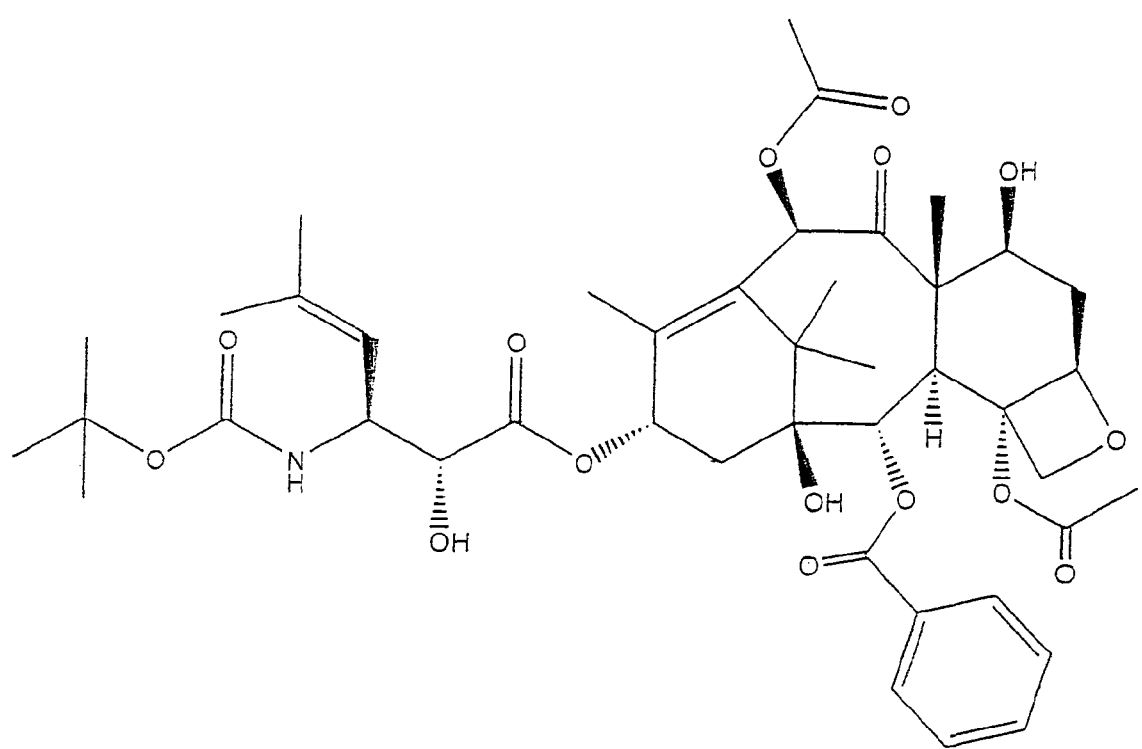
Figure 24:
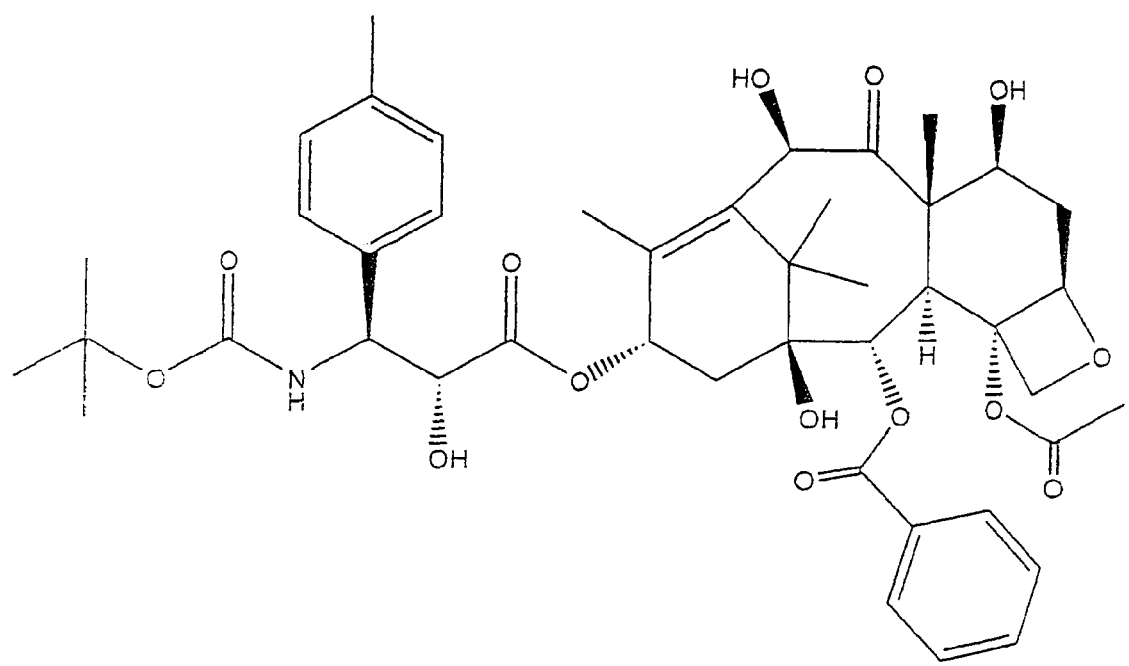
Figure 25:
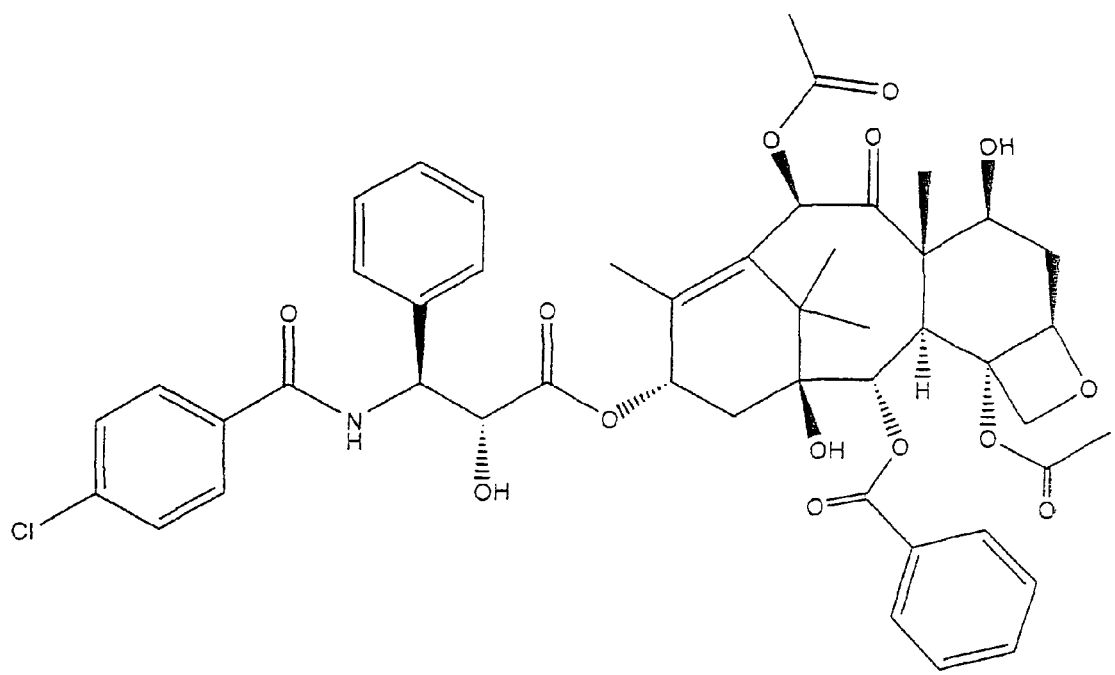

Paclitaxel, also referred to as "TAXOL", is a well-known anti-cancer drug which acts by inhibiting microtubule formation. Many analogs of paclitaxel are known, including docetaxel, the structure of which is shown in FIG. 4. Docetaxel is also referred to as "TAXOTERE". The structure of other paclitaxel analogs are shown in FIGS. 5-25. These compounds have the basic taxane skeleton as a common structure feature and have also been shown to have the ability to arrest cells in the G2-M phases due to stabilized microtubules. Thus, it is apparent from FIGS. 5-25 that a wide variety of substituents can decorate the taxane skeleton without adversely affecting biological activity. It is also apparent that zero, one or both of the cyclohexane rings of a paclitaxel analog can have a double bond at the indicated positions. For clarity purposes, the basic taxane skeleton is shown below in Structural Formula (VII):

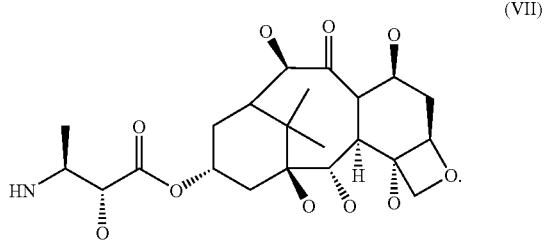

(VII)

Double bonds have been omitted from the cyclohexane rings in the taxane skeleton represented by Structural Formula (VII). It is to be understood that the basic taxane skeleton can include zero or one double bond in one or both cyclohexane rings, as indicated in FIGS. 5-25 and Structural Formulas (VIII) and (IX) below. A number of atoms have also omitted from Structural Formula (VII) to indicate sites in which structural variation commonly occurs among paclitaxel analogs. For example, substitution on the taxane skeleton with simply an oxygen atom indicates that hydroxyl, acyl, alkoxy or other oxygen-bearing substituent is commonly found at the site. It is to be understood that these and other substitutions on the taxane skeleton can also be made without losing the ability to enhance and stabilize microtubule formation. Thus, the term "paclitaxel analog" is defined herein to mean a compound which has the basic paclitaxel skeleton and which promotes disassembly of microtubules.

Typically, the paclitaxel analogs used herein are represented by Structural Formula (VIII) or (IX):

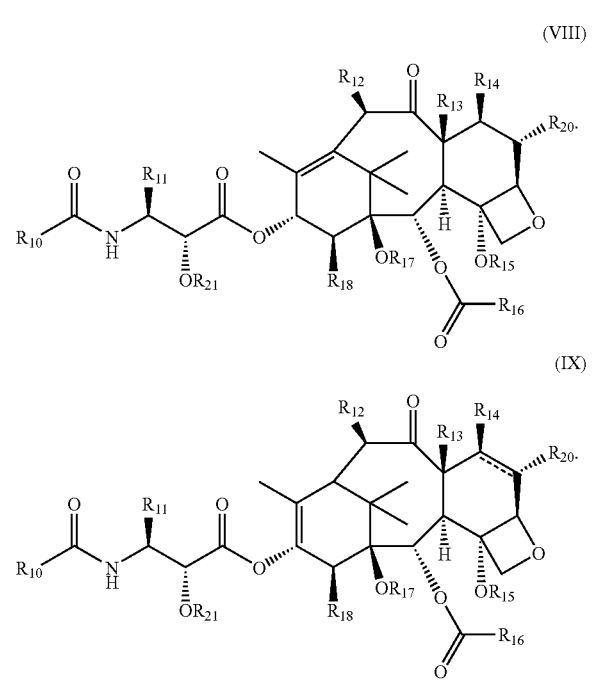

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl) —S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH(lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VIII) and (IX) are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH=C(CH$_3$)$_2$ or para-chlorophenyl; $R_{11}$ is phenyl, (CH$_3$)$_2$CHCH$_2$—, -2-furanyl, cyclopropyl or para-toluoyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 26:
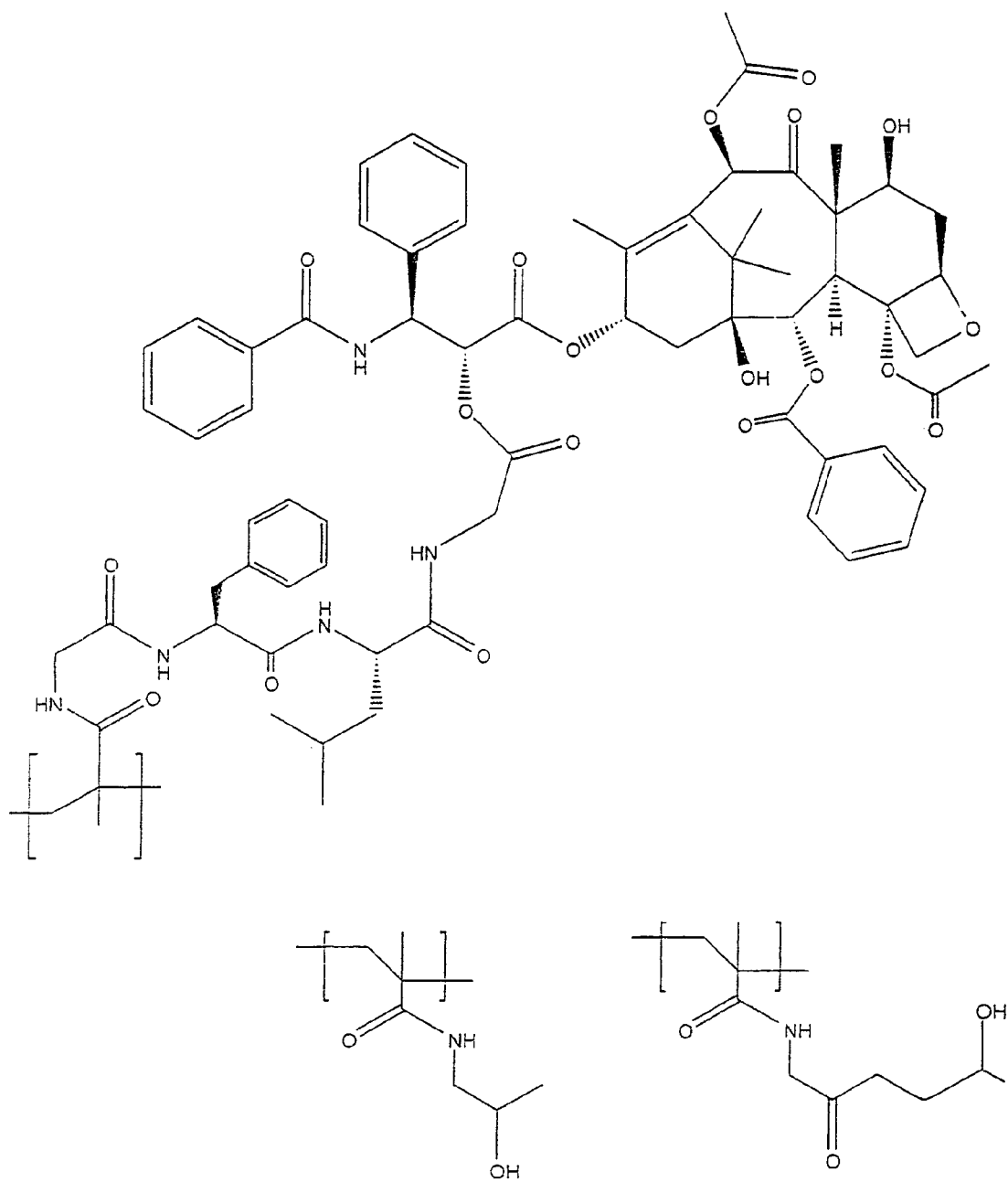
FIG. 26 is the structure of a polymer comprising a paclitaxel analog group pendent from the polymer backbone. The polymer is a terpolymer of the three monomer units shown.

A paclitaxel analog can also be bonded to or be pendent from a pharmaceutically acceptable polymer, such as a polyacrylamide. One example of a polymer of this type is shown in FIG. 26. The term "paclitaxel analog", as it is used herein, includes such polymers.

The disclosed compounds are enhancers of the anti-cancer activity of paclitaxel and paclitaxel analogs. A compound enhances the anti-cancer activity of paclitaxel or a paclitaxel analog when the activity of paclitaxel or the paclitaxel analog is greater when administered in combination with the compound than when administered alone. The degree of the increase in activity depends upon the amount of compound administered. The compounds of the present invention can therefore be used in combination with paclitaxel or paclitaxel analogs to treat subjects with cancers. Examples include colon cancer, pancreatic cancer, melanoma, renal cancer, sarcoma, breast cancer, ovarian cancer, lung cancer, stomach cancer, bladder cancer and cervical cancer.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In order to achieve an enhancement of the anti-cancer activity of paclitaxel and paclitaxel analogs, an effective amount of a compound of the present invention and an effective amount of paclitaxel or analog of paclitaxel are administered to the subject. With respect to paclitaxel or an analog of paclitaxel, an "effective amount" is a quantity in which anti-cancer effects are normally achieved. With respect to a compound of the present invention, an "effective amount" is the quantity in which a greater anti-cancer effect is achieved when the compound is co-administered with paclitaxel or a paclitaxel analog compared with when paclitaxel or the paclitaxel analog is administered alone. The compound and paclitaxel (or paclitaxel analog) can be co-administered to the subject as part of the same pharmaceutical composition or, alternatively, as separate pharmaceutical compositions. When administered as separate pharmaceutical compositions, the compound or the present invention and paclitaxel (or paclitaxel analog) can be administered simultaneously or at different times, provided that the enhancing effect of the compound is retained.

The amount of compound and paclitaxel (or paclitaxel analog) administered to the subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective dosages for paclitaxel and paclitaxel analog are well known and typically range from between about 1 mg/mm$^2$ per day and about 1000 mg/mm$^2$ per day, preferably between about 10 mg/mm$^2$ per day and about 500 mg/mm$^2$ per day. Effective amounts of a compound of the present invention typically range between about 1 mg/mm$^2$ per day and about 10 grams/mm$^2$ per day, and preferably between 10 mg/mm$^2$ per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration. Suitable routes of administration of paclitaxel and paclitaxel analogs are well known in the art and include by parenteral administration, as described above for the compounds of the present invention. Suitable routes of administration for paclitaxel and analogs thereof are well known and include inter alia parenteral and oral administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986). Suitable formulations for paclitaxel and paclitaxel analogs are well known in the art.

The disclosed compounds can be prepared according to methods described in Examples 1-12 and also according to methods described in the co-pending US Provisional Application entitled SYNTHESIS OF TAXOL ENHANCERS, U.S. Provisional Application No. 60/304,318, filed Jul. 10, 2001. The entire teachings of this application are incorporated herein by reference.

The present invention is illustrated by the following examples, which are not intended to be limiting in any way.

EXEMPLIFICATION

Example 1

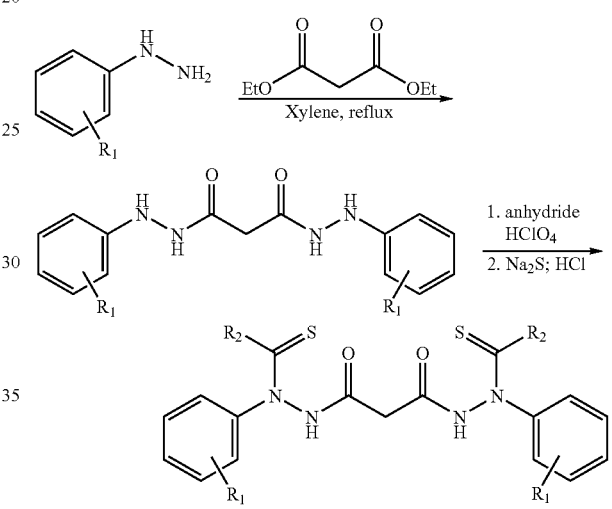

Preparation of N-Malonyl-bis[N'-phenyl-N'-(thio-acetyl)hydrazide]

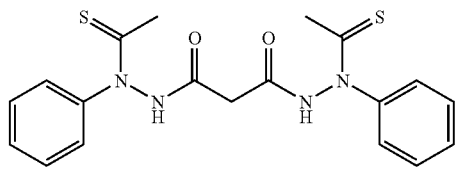

A mixture of phenylhydrazine (30 mL) and ethyl malonate (in xylene (150 mL) was heated to reflux overnight. The reaction was cooled to room temperature. The precipitates were collected via filtration and washed with ethanol to give N-malonyl-bis(N'-phenylhydrazide) as a white solid (14 g). The hydrazide (3.4 g) was suspended in acetic anhydride (30 mL) and cooled in an ice bath. To it was added dropwise perchloric acid (57% in water, 3 mL). The reaction mixture turned to clear solution initially and then quickly solidified. After standing at room temperature for 1 h, ether (50 mL) was added. The resulting slurry was filtered and washed with ether (2×00 mL) to give the perchlorate salts as a white solid (5.7 g). The salts were taken into acetone and added as a slurry over 5 min to Na$_2$S (0.6 M in water, 90 mL) stirred at room temperature. After 30 min, the reaction was acidified with HCl(c) to afford a yellow slurry. The solid was collected via filtration and washed with water (20 mL) and ether (2×25 mL) to give N-malonyl-bis[N'-phenyl-N'-(thioacetyl)hydrazide] as an off-white solid (3.6 g). $^1$H NMR (DMSO-d6): δ 11.5 (m, 2H); 7.5 (m, 10H); 3.2 (m, 2H); 2.6 (s, 3H); 2.5 (s, 3H). MS calcd (400.1); Found: 423.1 (M+Na)$^+$.

Example 2

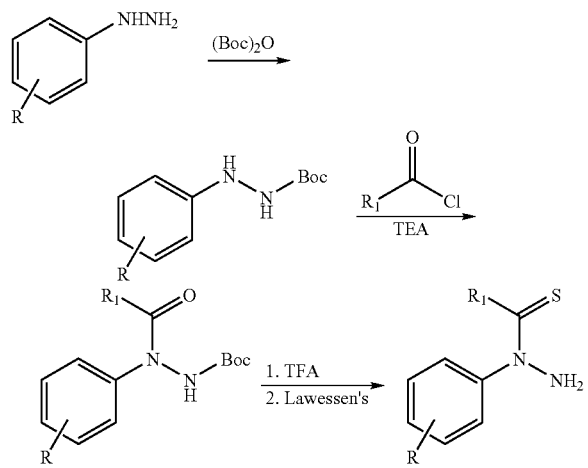

Preparation of Thiocyclohexanoic Acid N-phenylhydrazide

Phenyl hydrazine (5.4 g, 50 mmol) was dissolved in dry dichloromethane (50 mL) in a 250 mL round bottom flask. Di-tert-butyl dicarbonate (10.9 g, 50 mmol) was then added with stirring at 0° C. The resultant solution was then stirred under reflux for 3 h. Removal of the volatile components under reduced pressure afforded a colorless solid, which was washed with hexane and dried in vacuo. 10 g (yield 96%) of the product was obtained as a colorless solid, which can be used in the next step without further purification. 2.5 g (12 mmol) of this material was dissolved in dry pyridine (5 mL). Cyclohexanecarbonyl chloride (2.0 mL, 15 mmol) was then added slowly at 0° C. The red solution was stirred at 0° C. for half an hour and the resultant yellow suspension was stirred at rt for 3 h before pouring into ice-H$_2$O (100 mL). The precipitate product was collected by filtration and washed thoroughly with H$_2$O. After one recrystallization from EtOH/ H$_2$O, 3.63 g (95%) of N-phenyl-N-cyclohexyl-N'-tert-butoxycarbonylhydrazide was obtained as a white powder; mp 141-143° C.; $^1$H NMR (CDCl$_3$) δ 0.9-2.3 (m, 11H), 1.4 (s, 9H), 6.9 (br, 1H), 7.4 (m, 5H) ppm.

To a solution of N-phenyl-N-cyclohexyl-N'-tert-butoxycarbonylhydrazide (1.1 g, 3.46 mmol) in dichloromethane (6 mL) was added trifluoroacetic acid (6 mL) at 0° C. The resultant solution was stirred at 0° C. for half an hour. Volatile components were then removed under reduced pressure to afford a syrup, which was turned into a solid upon standing; this material was briefly mixed with cold 2 N NaOH (5 mL) for a few minutes at 0° C. Solid product was then collected by filtration and recrystallized from hexane to afford cyclohexanoic acid N-phenylhydrazide (0.6 g, 80% yield) as a white powder; $^1$H NMR (DMSO-d$_6$) δ 0.8-3.2 (m, 1H), 5.3 (s, 2H), 7.0-7.7 (m, 5H); ESMS calcd (C$_{13}$H$_{18}$N$_2$O): 218.3; found: 241.1 (M+Na)$^+$.

A mixture of cyclohexanoic acid N-phenylhydrazide (0.25 g, 1.15 mmol) and Lawesson's Reagent (0.46 g, 1.15 mmol) in dry toluene (20 mL) was stirred under reflux for 1 h. After being cooled to room temperature, the mixture was filtered through a short column of silica gel (5 g) which was pre-washed with benzene. Removal of benzene afforded the crude product as a solid which was purified by column chromatography on silica gel using hexane/EtOAc (4:1 v/v) as eluant. 0.15 g (60%) of thiocyclohexanoic acid N-phenylhydrazide was obtained as an off white solid. $^1$H NMR (CDCl$_3$) δ 0.8-2.4 (m, 1H), 5.65 (br, 1H), 7.1-7.6 (m, 5H); ESMS calcd (C$_{13}$H$_{18}$N$_2$S): 234.1; found: 235.1 (M+H)$^+$.

Example 3

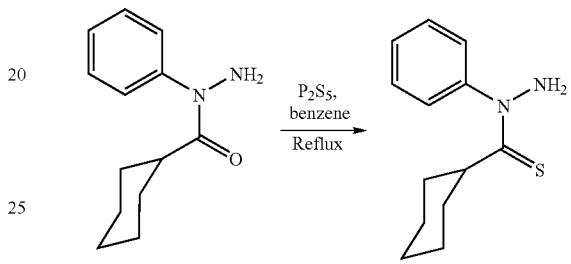

To a stirred solution of cyclohexanoic acid N-phenylhydrazide (0.1 g, 0.45 mmol) in dry benzene (5 mL) was added P$_2$S$_5$ (0.2 g, 0.45 mol). The resultant suspension was heated to reflux for 3 h. After being cooled to room temperature, the mixture was diluted with benzene (5 mL) and was filtered through a short column of silica gel (2 g), washed with benzene and 2:1 hexane/EtOAc (15 mL each). The filtrate and washings were combined and concentrated to afford a solid. Crystallized from hexane to provide the intermediate thiocyclohexanoic acid N-phenylhydrazide as an off white solid; $^1$H NMR (CDCl$_3$) δ 0.8-2.4 (m, 11H), 5.65 (br, 1H), 7.1-7.6 (m, 5H); ESMS calcd (C$_{13}$H$_{18}$N$_2$S): 234.1; found: 235.1 (M+H)$^+$.

Example 4

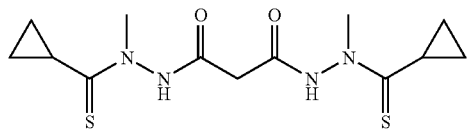

Cyclopropyl bromide (4.8 g, 40 mmol) was added into 50 ml anhydrous THF solution containing magnesium powder (1.1 g, 45 mmol), stirred for 30 min, and refluxed for another 30 min. After it was cooled, the clear reaction solution was added into carbon disulfide (4 ml, 67 mmol) at 0° C., and stirred for 30 min at rt. The resulting mixture was then added into methylhydrazine (8 ml, 150 mmol) at 0° C., and stirred for another 2 hours. To this solution was added water (40 ml) and extracted with EtOAc (60 ml×3). The organic solution was concentrated to minimum volume, and subjected to silica gel column chromatography (1:1 ethyl acetate:hexanes; ethyl acetate) to give thiocyclopropyl carboxylic acid N$^1$-methyl hydrazide (2.8 g, 55%). $^1$H NMR (300 MHz, CDCl$_3$): δ 5.21 (br., 2H), 3.62 (s, 3H), 1.91 (m, 1H), 1.25 (m, 2H), 0.98 (m, 2H). ESMS cacld (C$_5$H$_{10}$N$_2$S): 130.1; found: 131.1 (M+H)$^+$.

To the hydrazide EtOAc solution (2.8 g, 22 mmol, 40 ml)

containing TEA (2.2 g, 22 mmol) was added malonyl chloride EtOAc solution (1.6 g, 11 mmol, 4 ml) at 0° C., and the reaction mixture was stirred at rt for 20 min. 20 ml water was added to quench the reaction, and the EtOAc layer was continuously washed twice with water (20 ml×2). The EtOAc solution was concentrated to minimum volume, and subjected to silica gel column chromatography (eluant: 1:1-1:2 hexanes:ethyl acetate) to give SBR-11-5685 (2.1 g, yield: 60%). (2.1 g, yield: 60%). $^1$H NMR (300 MHz, CDCl$_3$): δ 10.01-8.95 (m, 2H), 3.78-3.41 (m, 6H), 2.34-0.82 (m, 10H). ESMS cacld ($C_{13}H_{20}N_4O_2S_2$): 328.1; found: 327 (M−H)$^+$.

Example 5

Preparation of 2-Methylmalonyl-bis(2-Amino-2,3-dihydro-isoindole-1-thione)

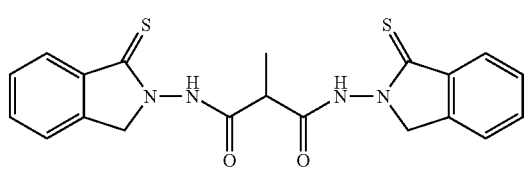

2-carboxybenzaldehyde (150 mg, 1 mmol) and carbazic acid (132 mg, 1 mmol) in 40 ml methanol was stirred at room temperature for 4 h. To this solution was added Pd/C (60 mg, containing 50% H$_2$O), the reaction was under H$_2$ atmosphere for 3 h. The reaction mixture was filtered, and the solvent was evaporated. The resulting residue was subjected to silica gel column chromatography. (eluent: 20% to 50%, EtOAc in hexanes) to obtain 50 mg of product. $^1$H NMR (300 MHz, CDCl$_3$): δ 8.71-7.45 (m, 4H), 4.78 (s, 2H), 1.61 (s, 9H). The resulting product was dissolved in CF$_3$COOH (5 ml), stirred for 30 min. The CF$_3$COOH was evaporated, and the residue was subjected to silica gel column chromatography (eluent: 50% to 0%, hexanes in EtOAc) to give 2-amino-2,3-dihydro-isoindol-1-one (26 mg) as a white solid. $^1$H NMR (300 MHz, CDCl$_3$): δ 7.85-7.39 (m, 4H), 4.54 (s, 2H). MS: 149 (M+H). Subsequent Lawesson's thiolation and DCC coupling with 2-methylmaloic acid under conditions described above afforded 2-methylmalonyl-bis(2-amino-2,3-dihydro-isoindole-1-thione) as a yellow powder. $^1$H NMR (CDCl$_3$) δ 10.35 (s, 2H), 8.21-7.51 (m, 8H), 5.15 (s, 4H), 1.62 (s, 3H); ESMS cacld ($C_{20}H_{18}N_4O_2S_2$): 410.09; found: 411.1 (M+H).

Example 6

The following compounds shown below were prepared by the procedures described above. Analytical data is provided for these compounds.

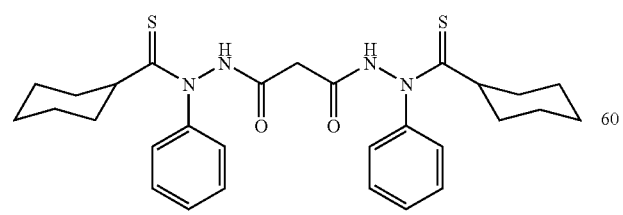

$^1$H NMR (DMSO-d$_6$) δ 0.9-1.8 m, 22H), 3.1-3.5 (m, 2H), 7.2-7.6 (m, 10H), 11.1-11.7 (ms, 2H) ppm; ESMS cacld ($C_{29}H_{36}N_4O_2S_2$): 536.3; found: 537.3 (M−H)$^+$.

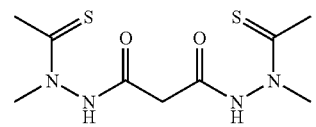

$^1$H NMR (CDCl$_3$): δ 3.6-3.4 (m, 8H), 2.7-2.5 (m, 6H); ESMS cacld for $C_9H_{16}N_4O_2S_2$: 276.1; Found: 274.9 (M−H)$^+$.

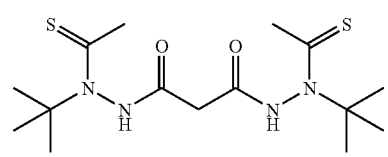

$^1$H NMR (CDCl$_3$): δ 2.63 (s, 2H); 2.18 (s, 6H); 1.25 (s, 18H). MS calcd for $C_{15}H_{28}N_4O_2S_2$: 360.2; Found: 383.1 (M+Na)$^+$.

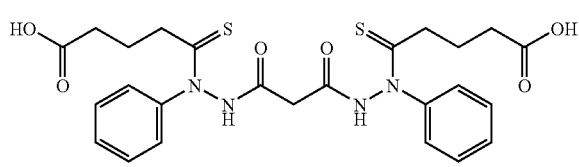

$^1$H NMR (CDCl$_3$): δ 7.3 (m, 10H); 3.2 (m, 2H); 2.45 (t, J=7.4 Hz, 4H); 2.21 (t, J=7.4 Hz, 4H); 1.90 (m, 8H). MS calcd for $C_{25}H_{28}N_4O_6S_2$: 544.15; Found: 567.2 (M+Na)$^+$.

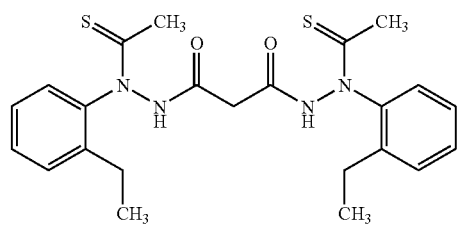

$^1$H NMR (CDCl$_3$): δ 7.8-7.4 (br s, 8H), 3.75-3.5 (m, 2H), 3.95-3.8 (m, 4H), 2.58 (s, 6H), 1.4 (m, 6H). ESMS cacld for $C_{23}H_{28}N_4O_2S_2$: 456.2; Found: 479.2 (M+Na).

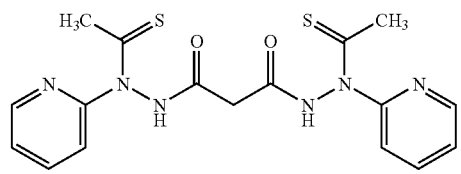

$^1$H NMR (CDCl$_3$): δ 8.3-8.05 (m, 4H), 7.75 (t, J=8.0 Hz, 2H), 7.1 (br s, 2H), 3.74 (s, 2H), 2.38 (s, 6H). ESMS cacld for $C_{17}H_{18}N_6O_2S_2$: 402.1. Found: 403.1 (M+H)$^+$.

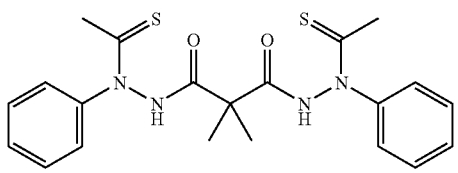

¹H NMR (CDCl₃): δ 7.38 (m, 10H), 2.40 (s, 6H), 1.5-1.6 (6H); ESMS cacld for $C_{21}H_{24}N_4O_2S_2$: 564.1; Found: 565.2 (M+H)⁺.

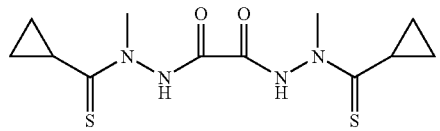

The method was the same as one used in synthesis of 4783, oxalyl chloride was used instead of malonyl dichloride. ¹H NMR (300 MHz, DMSO): δ 11.95 (s, 2H), 7.48-7.07 (m, 10H), 3.52 (s, 6H). ESMS cacld ($C_{18}H_{18}N_4O_2S_2$): 386.09; found: 387 (M+H)⁺.

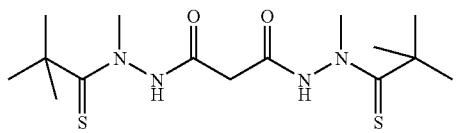

¹H NMR (300 MHz, CDCl₃): δ 9.66-8.83 (m, 2H), 3.73-3.23 (m, 6H), 2.10-1.20 (m, 20H). ESMS cacld ($C_{15}H_{28}N_4O_2S_2$): 360.17; found: 359 (M–H)⁺.

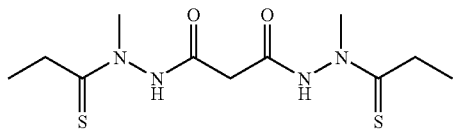

¹H NMR (300 MHz, CDCl₃): δ 3.66-3.42 (m, 6H), 2.84-2.58 (m, 4H), 1.40-1.19 (m, 6H). ESMS cacld ($C_{11}H_{20}N_4O_2S_2$): 304.10; found: 303 (M–H)⁺.

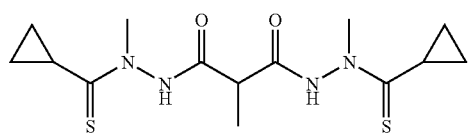

¹H NMR (300 MHz, CDCl₃): δ 4.15-3.40 (m, 6H), 2.00-1.01 (m, 14H). ESMS cacld ($C_{14}H_{22}N_4O_2S_2$): 342.12; found: 341 (M–H)⁺.

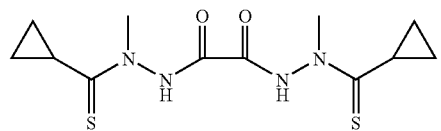

¹H NMR (300 MHz, CDCl₃): δ 3.90-3.18 (m, 6H), 2.11-0.91 (m, 10H). ESMS cacld ($C_{12}H_{18}N_4O_2S_2$): 314.09; found: 313 (M–H)⁺.

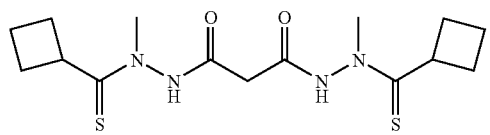

¹H NMR (300 MHz, CDCl₃): δ 10.08-9.01 (m, 2H), 3.68-3.20 (m, 6H), 2.59-1.12 (m, 16H). ESMS cacld ($C_{15}H_{24}N_4O_2S_2$): 356.13; found: 355 (M–H)⁺.

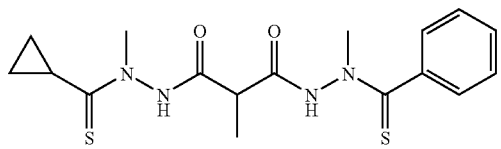

¹H NMR (300 MHz, CDCl₃): δ 10.22-9.41 (m, 2H), 7.48-7.20 (m, 5H), 3.82-3.02 (m, 6H), 2.38-0.82 (m, 7H). ESMS cacld ($C_{16}H_{20}N_4O_2S_2$): 364.10; found: 363 (M–H)⁺.

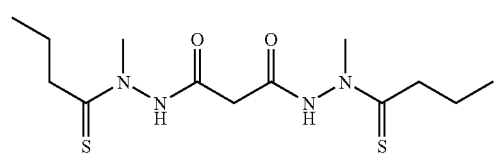

¹H NMR (300 MHz, CDCl₃): δ 10.03-9.02 (m, 2H), 3.71-3.42 (m, 6H), 2.80-0.81 (m, 16H). ESMS cacld ($C_{13}H_{24}N_4O_2S_2$): 332.13; found: 331 (M–H)⁺.

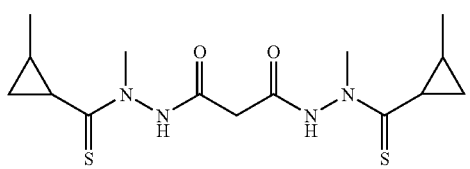

¹H NMR (300 MHz, CDCl₃): δ 3.78-3.08 (m, 6H), 1.90-0.81 (m, 18H). ESMS cacld ($C_{15}H_{24}N_4O_2S_2$): 356.13; found: 355 (M–H)⁺.

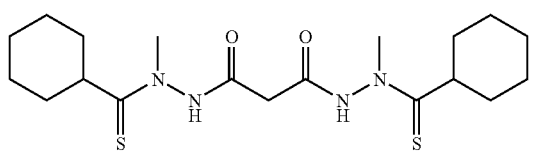

¹H NMR (300 MHz, CDCl₃): δ 10.00-8.79 (m, 2H), 3.65-3.07 (m, 6H), 2.79-1.08 (m, 24H). ESMS cacld ($C_{19}H_{32}N_4O_2S_2$): 412.20; found: 411 (M–H)⁺.

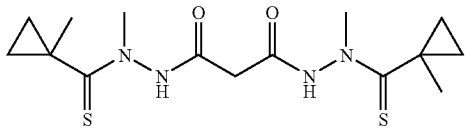

$^1$H NMR (300 MHz, CDCl$_3$): δ 9.79 (br, 2H), 3.79-3.41 (m, 6H), 1.60-0.75 (m, 18H). ESMS cacld (C$_{15}$H$_{24}$N$_4$O$_2$S$_2$): 356.13; found: 355 (M−H)$^+$.

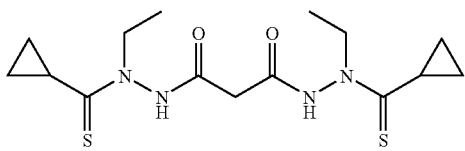

$^1$H NMR (300 MHz, CDCl$_3$): δ 10.03-9.14 (m, 2H), 4.21-3.39 (m, 4H), 2.20-0.76 (m, 18H). ESMS cacld (C$_{15}$H$_{24}$N$_4$O$_2$S$_2$): 356.13; found: 355 (M−H)$^+$.

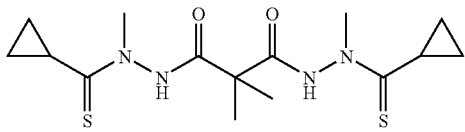

$^1$H NMR (300 MHz, CDCl$_3$): δ 7.57 (br, 2H), 3.72 (s, 6H), 2.95 (m, 6H), 1.96-0.81 (m, 10H). ESMS cacld (C$_{21}$H$_{36}$N$_4$O$_2$S$_2$): 440.13; found: 439 (M−H)$^+$.

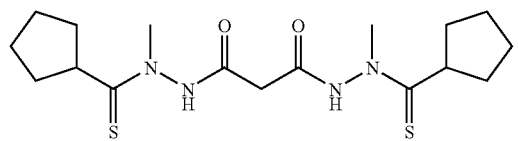

$^1$H NMR (300 MHz, CDCl$_3$): δ 10.09-8.95 (m, 2H), 3.78-3.05 (m, 6H), 2.04-1.22 (m, 20H). ESMS cacld (C$_{17}$H$_{28}$N$_4$O$_2$S$_2$): 384.17; found: 383 (M−H)$^+$.

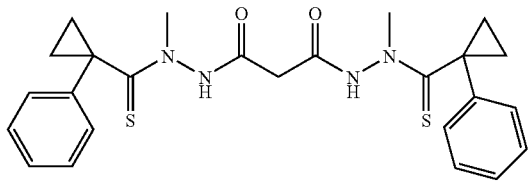

$^1$H NMR (300 MHz, CDCl$_3$): δ 10.09-8.51 (m, 2H), 7.41-7.01 (m, 10H), 3.62-3.02 (m, 6H), 1.78-1.03 (m, 10H). ESMS cacld (C$_{25}$H$_{28}$N$_4$O$_2$S$_2$): 480.17; found: 479 (M−H)$^+$.

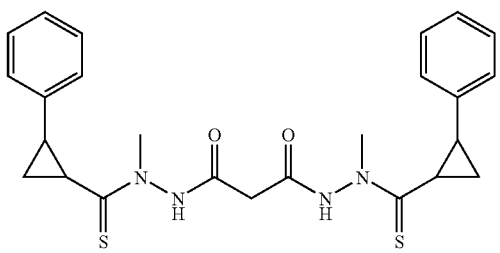

$^1$H NMR (300 MHz, CDCl$_3$): δ 10.09-8.81 (m, 2H), 7.51-7.11 (m, 10H), 3.80-3.06 (m, 6H), 2.92-1.53 (m, 10H). ESMS cacld (C$_{25}$H$_{28}$N$_4$O$_2$S$_2$): 480.17; found: 479 (M−H)$^+$.

Example 7

Compound (1) Enhances the Anti-Cancer Activity of Paclitaxel in Vivo (Human Xenograft Model: Human Breast Carcinoma MDA-435 in Nude Mice)

General Procedure of in Vivo Anti-Tumor Study

The in vivo anti-cancer enhancing effect of novel compounds was assessed in tumor bearing mice using the tumor growth inhibition assay. Tumor cells were implanted by injection of a tumor cell suspension subcutaneously in the flank of a mouse. Treatment of the tumor with an experimental compound and Paclitaxel began after the tumor had been established (volume was about 150 mm$^3$). Animal then begun a multiple injection schedule where the compound and Paclitaxel were given by IV route of administration. Tumors were measured two times a week. During the course of this assay, animals were monitored daily for signs of toxicity including body weight loss.

Detailed Procedure of MDA-435 (Human Breast Carcinoma) Anti-Tumor Study

A supplemented media was prepared from 50% DMEM/Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate and 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm2 tissue culture flask.

The cells used in the assay were MDA-435 Human Breast Carcinoma from the American Type Culture Collection. 1 vial of MDA-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm2 tissue culture flask containing supplemented media. The cells were incubated overnight and the media was removed and replaced with fresh supplemented media the next day. The flask was incubated until flask became about 90% confluent. This took anywhere from 5-7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2-3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1-3 million cells/flask were seeded into 5-7 tissue culture flasks (175 cm$^2$). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MDA-435, 100 million cells were suspended with 2.0 ml of sterile PBS to a final concentration of 50 million cells/ml in order to inject 5 million cells in 0.1 ml/mouse.

Mice (CD-1 nu/nu) were obtained from Charles River Laboratories: nomenclature: Crl:CD-1-nuBR, Age: 6-8 weeks. The mice were allowed to acclimate for 1 week prior to their being used in an experimental procedure.

Implantation of the MDA-435 tumor cell suspension took place into the corpus adiposum of the female CD-1 nu/nu mouse. This fat body is located in the ventral abdominal viscera of the mouse. Tumor cells were implanted subcutaneously into the fat body located in the right quadrant of the abdomen at the juncture of the os coxae (pelvic bone) and the os femoris (femur). 5 million MDA-435 cells in 0.1 ml of sterile PBS were injected using 27 G (½ inch) needle. MDA-435 tumors developed 2-3 weeks after implantation.

Compound stock solutions were prepared by dissolving the compound in a 50:50 mixture of EtOH and Cremophor EL (Polyoxyl 35 Castor Oil, BASF, Germany). This stock solution in 50% EtOH/50% CrEL was sonicated in an ultrasonic water bath until all the powder dissolved.

Preparation of Dosing Solution for Compound Administration: the Compound stock solution was diluted 1:10 with D5W (5% Dextrose in Water, Abbott Laboratories, USA). 1) 2.0 ml of 2.5 mg/ml dosing solution of Compound (1) was prepared by diluting 0.2 ml of a 25 mg/ml Compound Stock solution with 1.8 ml of 100% D5W; and 2) a dosing solution comprising of 1.5 mg/ml of Paclitaxel (obtained from Sigma Chemical Co.) and 2.5 mg/ml of Compound (1) was obtained by mixing 0.2 ml of a 50% EtOH/50% CrEL stock solution containing 25 mg/ml of Compound (1) and 15 mg/ml of Paclitaxel with 1.8 ml of a 100% D5W solution. The final formulation for the dosing solution was 5% EtOH, 5% CrEL, 4.5% Dextrose, and 85.5% water.

The Dosing Solution (Dosing Volume: 0.01 ml/gram=10 ml/kg) was injected intravenously into the mice bearing MDA-435 human breast tumor.

Protocol

Mice: CD-1 nu/nu female (n=5/group)

Tumor: MDA-435 (Human breast carcinoma)

Implantation: $5 \times 10^6$ cells/mouse

Formulation: 5% Cremophor EL, 5% ethanol, and 4.5% glucose water solution

Administration route: intravenous bolus injection

Dosing schedule: weekly×4

| Group | Drug Treatment (Dose) |
|---|---|
| 1 | Vechicle Only |
| 2 | Paclitaxel (15 mg/kg) |
| 3 | Compound (1) (25 mg/kg) |
| 4 | Paclitaxel (15 mg/kg) + Compound (1) (25 mg/kg) |

Results

Figure 2:
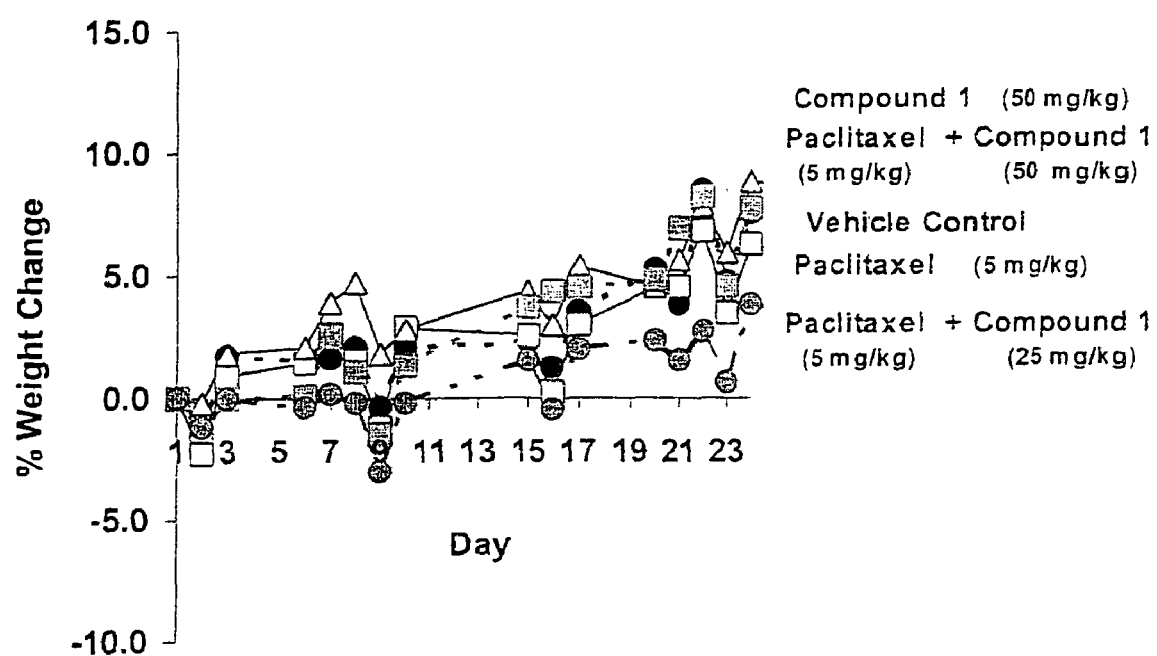
FIG. 2 is a graph showing the percent weight change over time in nude mice treated with vehicle (●); Compound (1) (25 mg/kg) (◆); Paclitaxel (15 mg/kg) (■); or Compound (1) (25 mg/kg) and Paclitaxel (15 mg/kg) (□). The mice were being treated for tumors generated from the human breast tumor cell line MDA-435.
Figure 3:
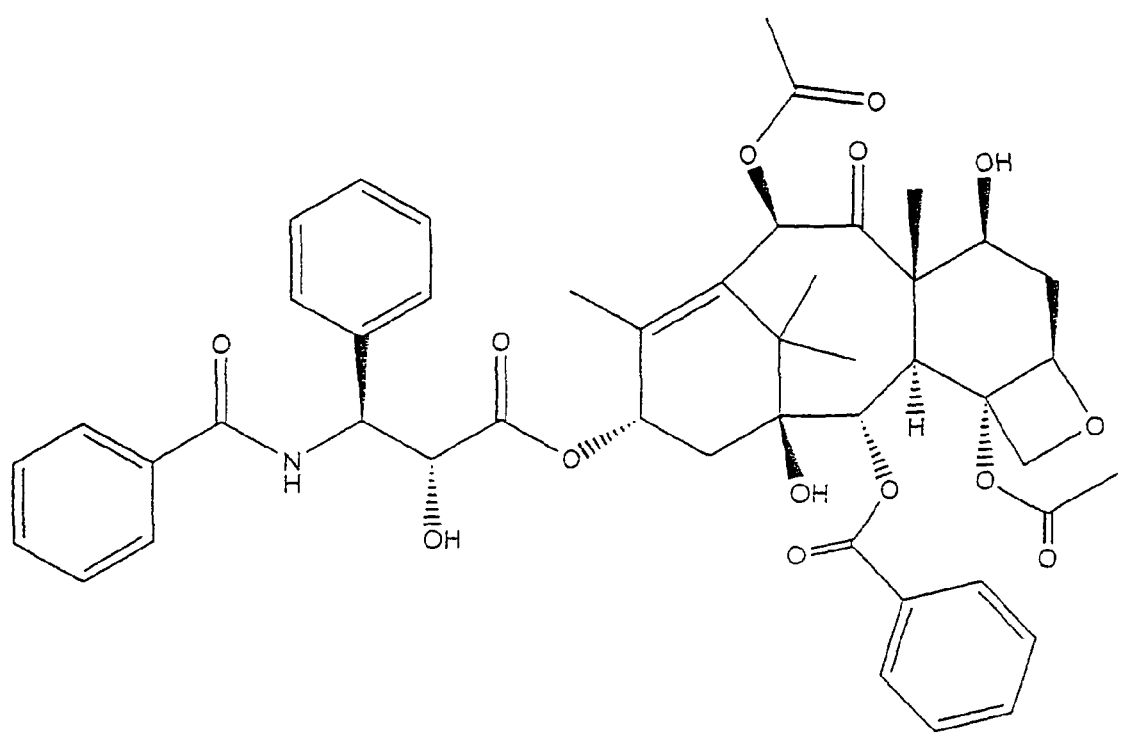
FIG. 3 is the structure of paclitaxel (TAXOL)

FIG. 1 shows the effects of Compound (1) on enhancing anti-tumor activity of Paclitaxel (TAXOL). As can be seen from FIG. 1, Compound (1) significantly enhanced anti-tumor activity of Paclitaxel on human breast tumor MDA-435 in nude mice. FIG. 2 shows the effects of Compound (1) and Paclitaxel on the body weight of nude mice bearing MDA-435 human breast tumor. As can be seen from FIG. 2, Compound (1) significantly enhanced anti-tumor activity of Paclitaxel without increasing toxicity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

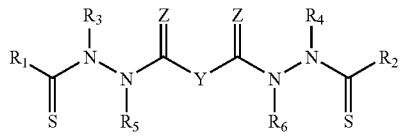

or a pharmaceutically acceptable salt thereof, wherein:
Y is a covalent bond or a substituted or unsubstituted straight chained hydrocarbyl group;
$R_1$ is an aliphatic group, a substituted aliphatic group, a non-aromatic heterocyclic ring, or a substituted non-aromatic heterocyclic ring;
$R_2$ is —H, an aliphatic group, a substituted aliphatic group, a non-aromatic heterocyclic ring, a substituted non-aromatic heterocyclic ring, an aryl group or a substituted aryl group;
$R_3$ and $R_4$ are independently an aliphatic group, a substituted aliphatic group, a non-aromatic heterocyclic ring, a substituted non-aromatic heterocyclic ring, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;
$R_5$-$R_6$ are independently —H, an aliphatic group, a substituted aliphatic group, an aryl group or a substituted aryl group; and
Z is =O or =S;
provided that when Y is —$CH_2$, $R_3$ and $R_4$ are both phenyl and $R_5$-$R_6$ are all —H, then $R_1$ and $R_2$ are not both methyl.

2. The compound of claim 1 wherein:
Y is a covalent bond or a substituted or unsubstituted straight chained hydrocarbyl group;
$R_1$ is an aliphatic group or a substituted aliphatic group;
$R_2$ is —H, an aliphatic group, a substituted aliphatic group, an aryl group or a substituted aryl group
$R_3$ and $R_4$ are independently an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

3. The compound of claim 2 wherein the compound is represented by the following structural formula:

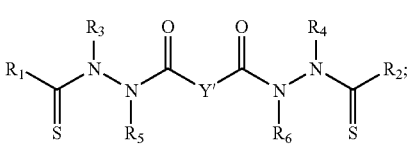

or a pharmaceutically acceptable salt thereof, wherein Y' is a covalent bond or —CR$_7$R$_8$— and R$_7$ and R$_8$ are each independently —H, an aliphatic or substituted aliphatic group, or R$_7$ is —H and R$_8$ is a substituted or unsubstituted aryl group, or, R$_7$ and R$_8$, taken together, are a C2-C6 substituted or unsubstituted alkylene group.

4. The compound of claim 1 wherein the compound is represented by the following structural formula:

$$R_1\!-\!\underset{S}{\overset{\underset{|}{R_3}}{C}}\!-\!\underset{\underset{R_5}{|}}{N}\!-\!\overset{O}{\overset{\|}{C}}\!-\!Y'\!-\!\overset{O}{\overset{\|}{C}}\!-\!\underset{\underset{R_6}{|}}{N}\!-\!\underset{S}{\overset{\underset{|}{R_4}}{C}}\!-\!R_2;$$

or a pharmaceutically acceptable salt thereof, wherein Y' is a covalent bond or —CR$_7$R$_8$—, at least one of R$_1$-R$_2$ is an aliphatic group, a substituted aliphatic group, a non-aromatic heterocyclic ring, or a substituted non-aromatic heterocyclic ring and R$_5$-R$_8$ are all —H.

5. The compound of claim 1 wherein the compound is represented by the following structural formula:

$$R_1\!-\!\underset{S}{\overset{\underset{|}{R_3}}{C}}\!-\!\underset{\underset{R_5}{|}}{N}\!-\!\overset{O}{\overset{\|}{C}}\!-\!Y'\!-\!\overset{O}{\overset{\|}{C}}\!-\!\underset{\underset{R_6}{|}}{N}\!-\!\underset{S}{\overset{\underset{|}{R_4}}{C}}\!-\!R_2;$$

wherein Y' is a covalent bond or —CR$_7$R$_8$—, at least one of R$_1$-R$_2$ is an unsubstituted C3-C8 cyclic aliphatic group, a substituted C3-C8 cyclic aliphatic group, a substituted straight chained or branched aliphatic group, a substituted non-aromatic heterocyclic ring, or an unsubstituted non-aromatic heterocyclic ring and R$_7$ and R$_8$ are each independently —H, an aliphatic or substituted aliphatic group, or R$_7$ is —H and R$_8$ is a substituted or unsubstituted aryl group, or, R$_7$ and R$_8$, taken together, are a C2-C6 substituted or unsubstituted alkylene group.

6. The compound of claim 3 wherein the compound is represented by the following structural formula:

$$R_1\!-\!\underset{S}{\overset{\underset{|}{R_3}}{C}}\!-\!\underset{H}{N}\!-\!\overset{O}{\overset{\|}{C}}\!-\!Y''\!-\!\overset{O}{\overset{\|}{C}}\!-\!\underset{H}{N}\!-\!\underset{S}{\overset{\underset{|}{R_4}}{C}}\!-\!R_2;$$

or a pharmaceutically acceptable salt thereof, wherein Y" is a covalent bond or —CH$_2$—.

7. The compound of claim 6 wherein R$_1$ and R$_2$ are the same.

8. The compound of claim 6 wherein the compound is represented by the following structural formula:

$$R_1\!-\!\underset{S}{\overset{\underset{|}{R_3}}{C}}\!-\!\underset{H}{N}\!-\!\overset{O}{\overset{\|}{C}}\!-\!Y''\!-\!\overset{O}{\overset{\|}{C}}\!-\!\underset{H}{N}\!-\!\underset{S}{\overset{\underset{|}{R_4}}{C}}\!-\!R_2;$$

or a pharmaceutically acceptable salt thereof, wherein Y" is a covalent bond or —CH$_2$— and R$_1$ is a substituted or unsubstituted aliphatic group and R$_2$ is a substituted or unsubstituted aryl group.

9. The compound of claim 6 wherein R$_1$ and R$_2$ are the same and R$_3$ and R$_4$ are the same.

10. The compound of claim 9 wherein R$_1$ and R$_2$ are both lower alkyl or a substituted lower alkyl groups.

11. The compound of claim 10 wherein R$_1$ and R$_2$ are both methyl, ethyl, n-propyl, n-butyl n-pentyl or cyclopropyl.

12. The compound of claim 10 wherein R$_1$ and R$_2$ are both 1-methylcyclopropyl, 2-methylcyclopropyl, cyclobutyl, cyclopentyl, or cyclohexyl.

13. The compound of claim 10 wherein R$_1$ and R$_2$ are both a C3-C8 cyclic alkyl group substituted with at least one lower alkyl group.

14. The compound of claim 9 wherein R$_1$ and R$_2$ are both a substituted or unsubstituted C3-C8 cyclic aliphatic group.

15. The compound of claim 14 wherein R$_1$ and R$_2$ are both a cyclopropyl group or a substituted cyclopropyl group.

16. The compound of claim 14 wherein R$_1$ and R$_2$ are both a C3-C8 cyclic aliphatic group substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHNR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, non-aromatic heterocyclic ring, benzyl group, aryl group wherein R$^a$-R$^d$ are each independently an alkyl group, benzyl, aromatic group, or, —N(R$^a$R$^b$), taken together, can also form a non-aromatic heterocyclic ring.

17. The compound of claim 1 wherein the compound is represented by the following structural formula:

$$R_1\!-\!\underset{S}{\overset{\underset{|}{R_3}}{C}}\!-\!\underset{H}{N}\!-\!\overset{O}{\overset{\|}{C}}\!-\!Y'\!-\!\overset{O}{\overset{\|}{C}}\!-\!\underset{H}{N}\!-\!\underset{S}{\overset{\underset{|}{R_4}}{C}}\!-\!R_2;$$

or a pharmaceutically acceptable salt thereof, wherein Y' is a covalent bond or —CR$_7$R$_8$—.

18. The compound of claim 17 wherein R$_7$ and R$_8$ are different.

19. The compound of claim 17 where R$_1$ and R$_2$ are the same; and R$_3$ and R$_4$ are the same.

20. A compound represented by the following structural formula:

or a pharmaceutically acceptable salt thereof, wherein:

Y' is a covalent bond or —CR$_7$R$_8$—;

R$_1$ and R$_2$ are both a substituted or unsubstituted aliphatic group;

R$_3$ and R$_4$ are both methyl or ethyl; and

R$_7$ is —H and R$_8$ is —H or methyl.

21. The compound of claim 20 wherein R$_1$ and R$_2$ are both C3-C8 cyclic aliphatic group substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$-C(=NH)—NHR$^a$, —NR$^d$-C(=NH)—N(R$^a$R$^b$), —NR$^d$-C(=NR$^c$)—NH$_2$, —NR$^d$-C(=NR$^c$)—NHR$^a$, —NR$^d$-C(=NR$^c$)—N(R$^a$R$^b$), —NHNH$_2$, —NHNHR$^a$, —NHNR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, non-aromatic heterocyclic ring, benzyl group, aryl group wherein R$^a$-R$^d$ are each independently an alkyl group, benzyl, aromatic group, or, —N(R$^a$R$^b$), taken together, can also form a non-aromatic heterocyclic ring.

22. The compound of claim 3 wherein R$_5$ and R$_6$ are the same.

23. The compound of claim 22 wherein the compound is represented by the following structural formula:

or a pharmaceutically acceptable salt thereof, wherein Y" is a covalent bond or —CH$_2$.

24. The compound of claim 23 wherein R$_5$ and R$_6$ are both a lower alkyl group or a phenyl group.

25. The compound of claim 24 wherein R$_5$ and R$_6$ are both a methyl group.

26. A compound represented by the following structural formula:

or a pharmaceutically acceptable salt thereof.

27. A compound represented by the following structural formula:

or a pharmaceutically acceptable salt thereof.

28. A pharmaceutical composition comprising a pharmaceutically acceptable carrier or diluent and a compound represented by the following structural formula:

or a pharmaceutically acceptable salt thereof, wherein:

Y is a covalent bond or a substituted or unsubstituted straight chained hydrocarbyl group;

R$_1$ is an aliphatic group, a substituted aliphatic group, a non-aromatic heterocyclic ring, or a substituted non-aromatic heterocyclic ring;

R$_2$ is —H, an aliphatic group, a substituted aliphatic group, a non-aromatic heterocyclic ring, a substituted non-aromatic heterocyclic ring, an aryl group or a substituted aryl group;

R$_3$ and R$_4$ are independently an aliphatic group, a substituted aliphatic group, a non-aromatic heterocyclic ring, a substituted non-aromatic heterocyclic ring, an aryl group or a substituted aryl group, or R$_1$ and R$_3$ taken together with the carbon and nitrogen atoms to which they are bonded, and/or R$_2$ and R$_4$ taken together with the carbon and nitrogen atoms to which they are bonded, form a non-aromatic heterocyclic ring optionally fused to an aromatic ring;

R$_5$-R$_6$ are independently —H, an aliphatic group, a substituted aliphatic group, an aryl group or a substituted aryl group; and Z is =O or =S;

provided that when Y is —CH$_2$, R$_3$ and R$_4$ are both phenyl and R$_5$R are all —H, then R$_1$ and R$_2$ are not both methyl.

29. The pharmaceutical composition of claim 28 wherein the compound is represented by the following structural formula:

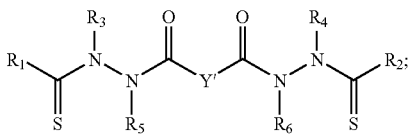

or a pharmaceutically acceptable salt thereof, wherein Y' is a covalent bond or —CR$_7$R$_8$—, at least one of R$_1$-R$_2$ is an unsubstituted C3-C8 cyclic aliphatic group, a substituted C3-C8 cyclic aliphatic group, a substituted straight chained or branched aliphatic group, a substituted non-aromatic heterocyclic ring, or an unsubstituted non-aromatic heterocyclic ring and R$_7$ and R$_8$ are each independently —H, an aliphatic or substituted aliphatic group, or R$_7$ is —H and R$_8$ is a substituted or unsubstituted aryl group, or, R$_7$ and R$_8$, taken together, are a C2-C6 substituted or unsubstituted alkylene group.

30. The pharmaceutical composition of claim 28 wherein the compound is represented by the following structural formula:

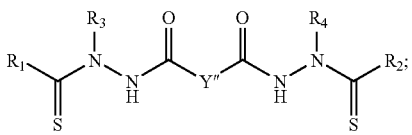

or a pharmaceutically acceptable salt thereof, wherein:
Y" is a covalent bond or —CH$_2$—;
R$_1$ is an aliphatic group or a substituted aliphatic group;
R$_2$ is —H, an aliphatic group, a substituted aliphatic group, an aryl group or a substituted aryl group; and
R$_3$ and R$_4$ are independently an aliphatic group, a substituted aliphatic group, an aryl group or a substituted aryl group, or R$_1$ and R$_3$ taken together with the carbon and nitrogen atoms to which they are bonded, and/or R$_2$ and R$_4$ taken together with the carbon and nitrogen atoms to which they are bonded, form a non-aromatic heterocyclic ring optionally fused to an aromatic ring.

31. The pharmaceutical composition of claim 28, wherein the compound is represented by the following structural formula:

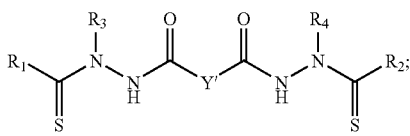

or a pharmaceutically acceptable salt thereof, wherein:
Y' is a covalent bond or —CR$_7$R$_8$—;
R$_1$ and R$_2$ are both a substituted or unsubstituted aliphatic group;
R$_3$ and R$_4$ are both methyl or ethyl; and
R$_7$ is —H and R$_8$ is —H or methyl.

32. The pharmaceutical composition of claim 28, wherein the compound is represented by a structural formula selected from:

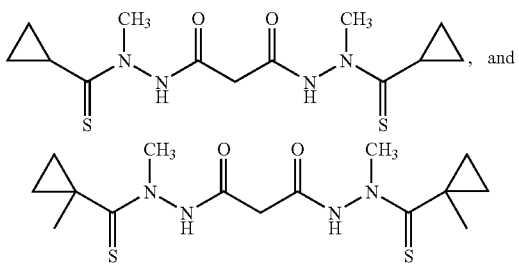

or a pharmaceutically acceptable salt thereof.

* * * * *